(12) United States Patent
Benning et al.

(10) Patent No.: US 11,109,848 B2
(45) Date of Patent: Sep. 7, 2021

(54) BIOPSY DEVICES AND RELATED METHODS OF USE

(71) Applicant: Boston Scientific Scimed, Inc., Maple Grove, MN (US)

(72) Inventors: Christopher A. Benning, Hopkinton, MA (US); Adam Charles Bechtold, Madison, CT (US); Scott E. Brechbiel, Acton, MA (US); Paul J. Smith, Smithfield, RI (US); Jeffrey V. Bean, Fitchburg, MA (US); John B. Golden, Norton, MA (US); Barry Weitzner, Acton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 437 days.

(21) Appl. No.: 15/820,892

(22) Filed: Nov. 22, 2017

(65) Prior Publication Data
US 2018/0140289 A1    May 24, 2018

Related U.S. Application Data

(60) Provisional application No. 62/425,763, filed on Nov. 23, 2016.

(51) Int. Cl.
*A61B 10/06* (2006.01)
*A61B 10/04* (2006.01)
(Continued)

(52) U.S. Cl.
CPC .......... *A61B 10/04* (2013.01); *A61B 10/0266* (2013.01); *A61B 10/0275* (2013.01); *A61B 10/06* (2013.01); *A61B 18/1482* (2013.01); *A61B 2010/0208* (2013.01); *A61B 2010/045* (2013.01); *A61B 2017/2936* (2013.01); *A61B 2017/2941* (2013.01); *A61B 2017/2944* (2013.01); *A61B 2018/00214* (2013.01); *A61B 2018/00595* (2013.01); *A61B 2018/1407* (2013.01); *A61B 2018/1465* (2013.01)

(58) Field of Classification Search
CPC combination set(s) only.
See application file for complete search history.

(56) References Cited

U.S. PATENT DOCUMENTS

| 4,763,669 A | * | 8/1988 | Jaeger | A61B 10/0291 30/251 |
| 5,133,727 A | * | 7/1992 | Bales | A61B 17/29 606/170 |

(Continued)

FOREIGN PATENT DOCUMENTS

| EP | 2 636 379 A1 | 9/2013 |
| EP | 2 745 781 A1 | 6/2014 |
| WO | 2008/029120 A1 | 3/2008 |

*Primary Examiner* — Puya Agahi
(74) *Attorney, Agent, or Firm* — Bookoff McAndrews, PLLC

(57) ABSTRACT

A biopsy device may include a first jaw having a first distal tip configured to pierce tissue, and a second jaw movable relative to the first jaw between a closed configuration where the first jaw and the second jaw are axially aligned, and an open configuration where the first jaw and the second jaw are offset from one another, the second jaw having a second distal tip proximal to the first distal tip in the closed configuration.

20 Claims, 15 Drawing Sheets

(51) Int. Cl.
*A61B 10/02* (2006.01)
*A61B 18/14* (2006.01)
A61B 18/00 (2006.01)
A61B 17/29 (2006.01)

(56) References Cited

U.S. PATENT DOCUMENTS

| | | | | |
|---|---|---|---|---|
| 5,141,519 | A | * | 8/1992 | Smith .................... A61B 17/29 |
| | | | | 606/205 |
| 5,389,104 | A | * | 2/1995 | Hahnen .............. A61B 17/1608 |
| | | | | 606/174 |
| 5,833,703 | A | * | 11/1998 | Manushakian .... A61B 17/2812 |
| | | | | 606/174 |
| 5,919,206 | A | | 7/1999 | Gengler et al. |
| 5,984,939 | A | * | 11/1999 | Yoon ................ A61B 17/12013 |
| | | | | 606/139 |
| 7,473,232 | B2 | | 1/2009 | Teague |
| 2006/0258954 | A1 | | 11/2006 | Timberlake et al. |
| 2007/0255311 | A1 | * | 11/2007 | Hiraoka ............. A61B 1/00137 |
| | | | | 606/205 |
| 2008/0004650 | A1 | * | 1/2008 | George .................. B26B 13/20 |
| | | | | 606/174 |
| 2010/0312140 | A1 | | 12/2010 | Smith et al. |
| 2012/0239011 | A1 | | 9/2012 | Hyodo et al. |
| 2016/0089208 | A1 | | 3/2016 | Vetter |

\* cited by examiner

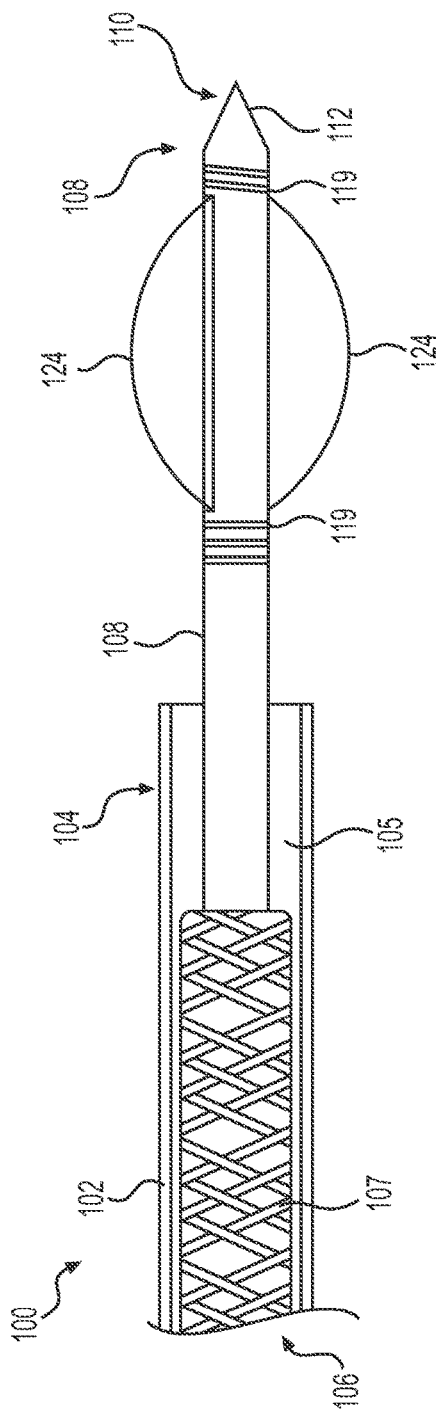
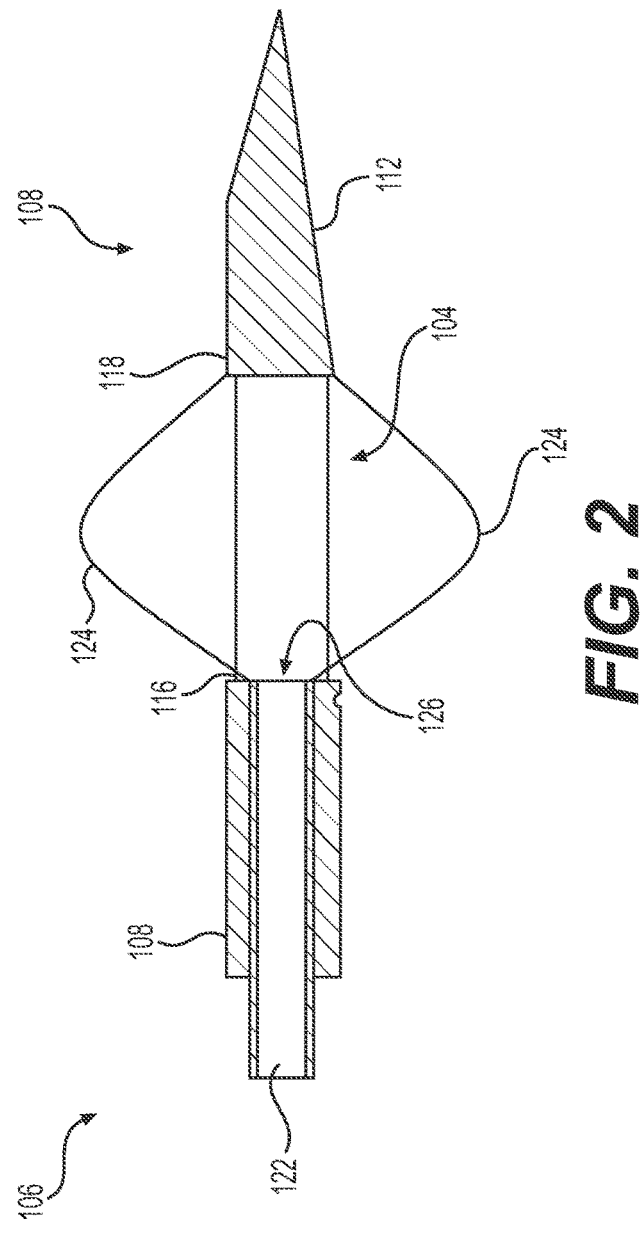
FIG. 1
FIG. 2

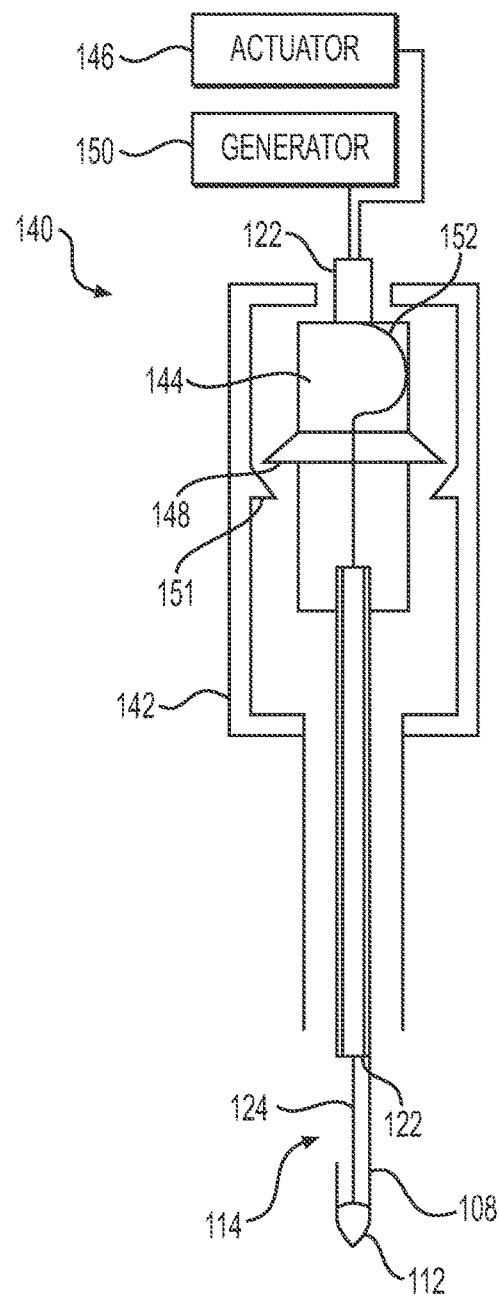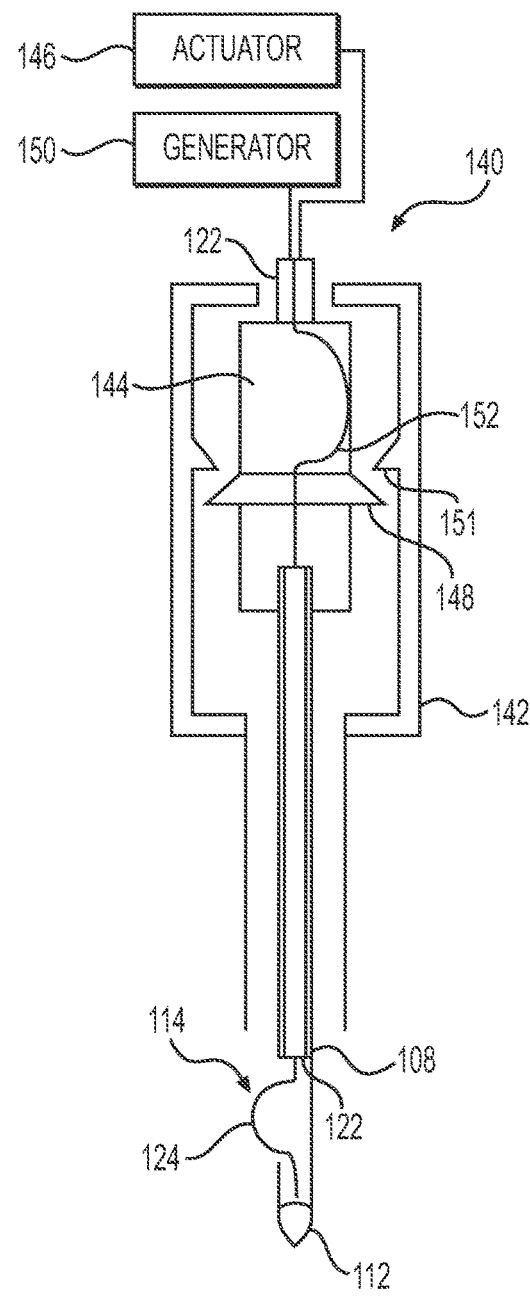
FIG. 5
FIG. 6

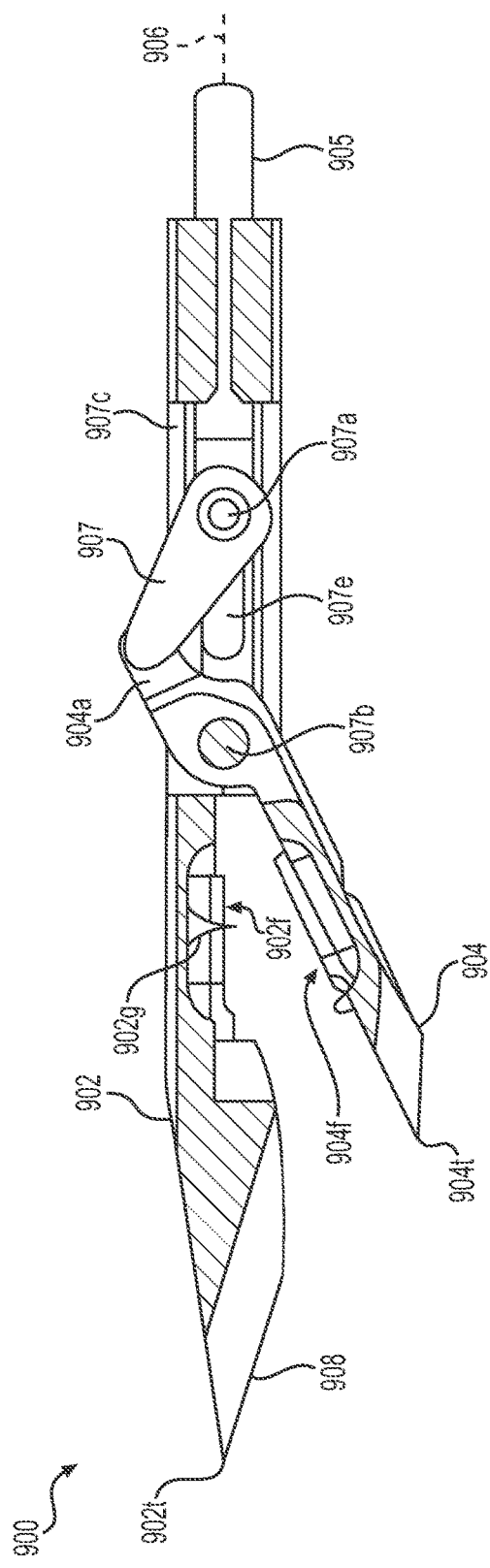
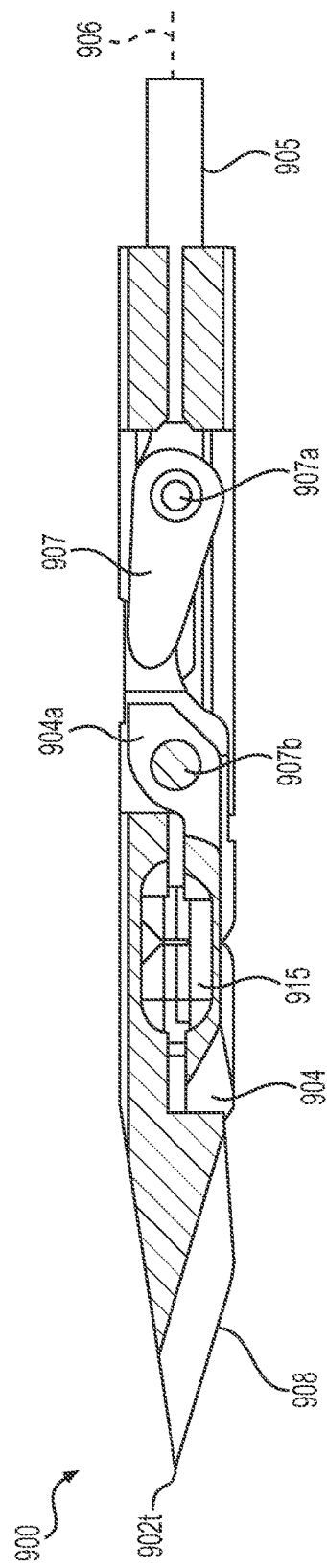
FIG. 9
FIG. 9A

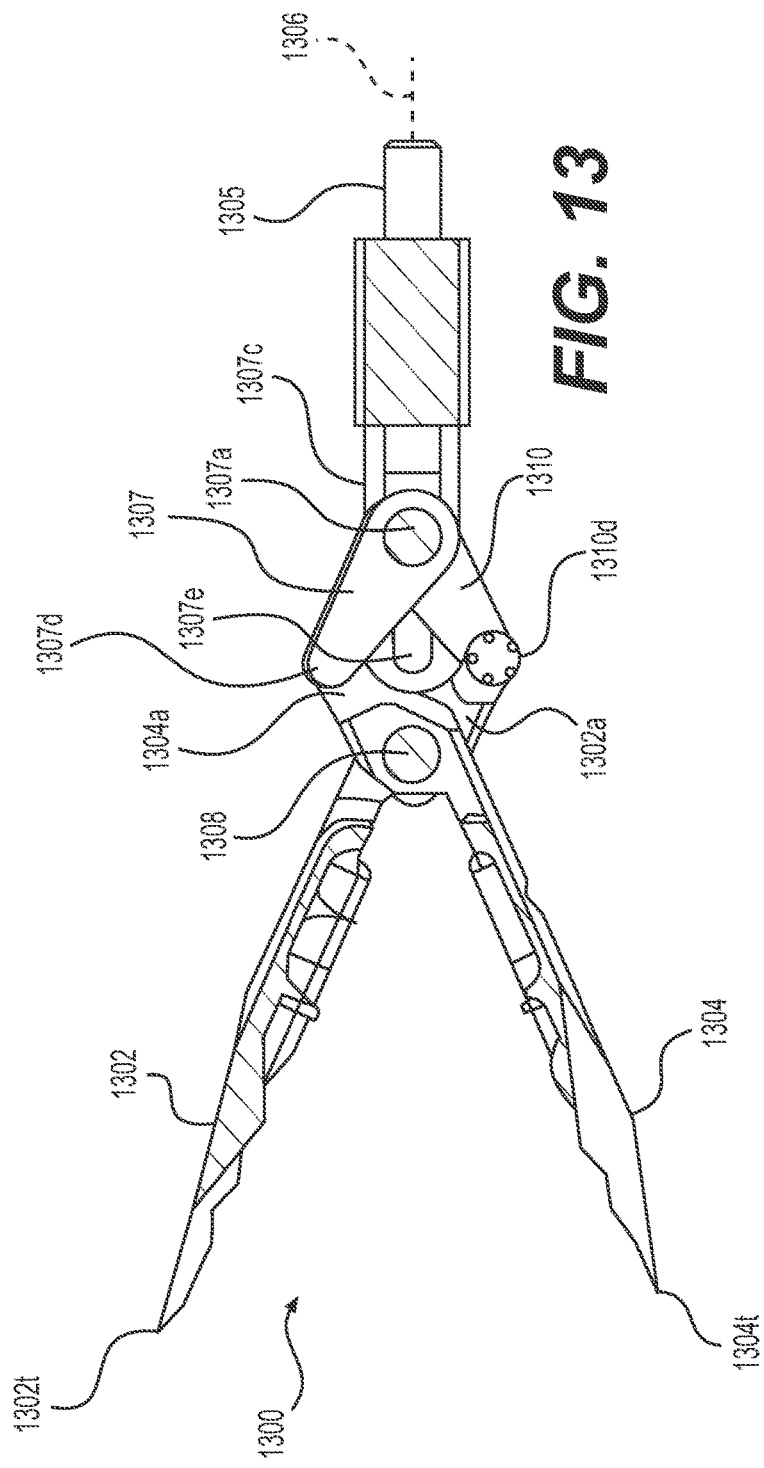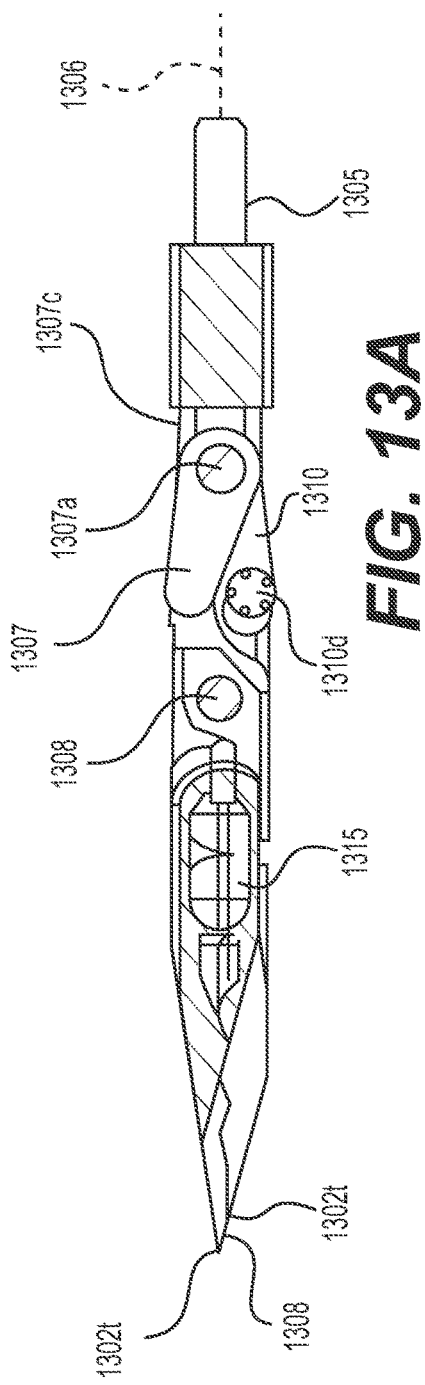

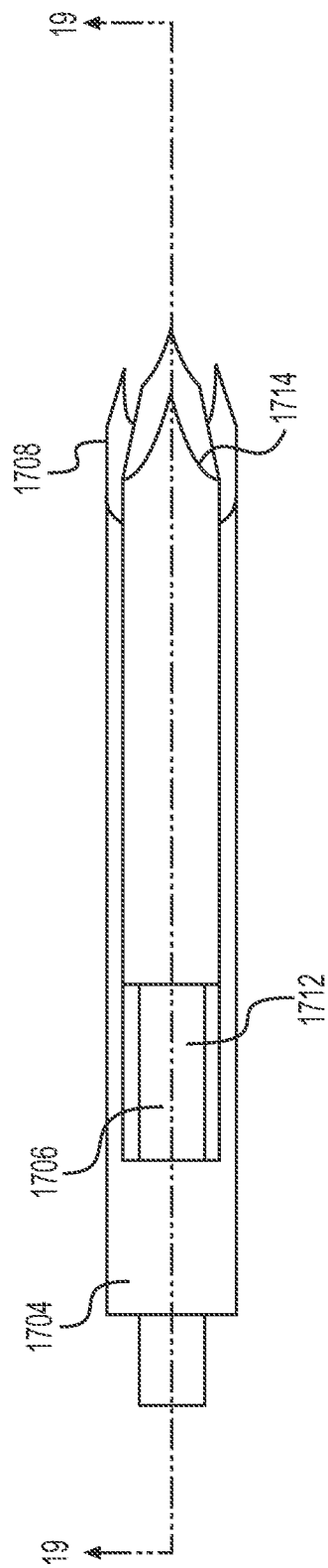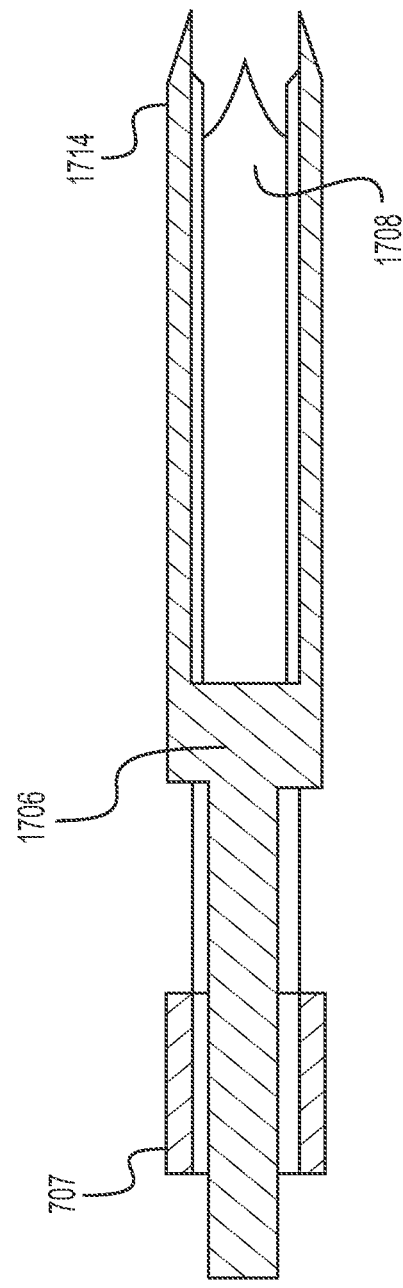
FIG. 18
FIG. 19

BIOPSY DEVICES AND RELATED METHODS OF USE

CROSS-REFERENCE TO RELATED APPLICATION(S)

This application claims the benefit under 35 U.S.C § 119(e) of U.S. Provisional Application No. 62/425,763, filed on Nov. 23, 2016, the entirety of which is incorporated by reference herein.

TECHNICAL FIELD

Various examples of the present disclosure relate generally to biopsy devices and related methods of use.

BACKGROUND

Physicians often need to take biopsies of growths located beyond the walls of a body lumen. Currently, fine needle aspiration (FNA) or biopsy needles are used to take coring samples of the growth tissue (e.g., cysts, nodules, infections, and inflammations, among others), and the tissue around it. One issue faced by these conventional devices is that the structure of certain tissues may make tissue samples difficult to acquire. Additionally, a substantial amount of non-targeted tissue is undesirably biopsied using conventional devices. Further, samples taken from traditional needle biopsies (e.g., coring) often fail to preserve the structure of the growth tissue, which could otherwise provide valuable diagnostic information. Still further, coring may be ill suited for taking samples of fibrous tumor tissue.

SUMMARY OF THE DISCLOSURE

In one aspect the present disclosure is directed to a biopsy device that may include a first jaw having a first distal tip configured to pierce tissue, and a second jaw movable relative to the first jaw between a closed configuration where the first jaw and the second jaw are axially aligned, and an open configuration where the first jaw and the second jaw are offset from one another, the second jaw having a second distal tip proximal to the first distal tip in the closed configuration.

When viewed from a position distal to the biopsy device along a central longitudinal axis of the biopsy device, the second distal tip may be concealed from view by the first jaw. When viewed from a position distal to the biopsy device along a central longitudinal axis of the biopsy device, the entirety of the second jaw may be concealed from view by the first jaw. When viewed from a position distal to the biopsy device along a central longitudinal axis of the biopsy device, both the first distal tip and the second distal tip may be in view. The first jaw may include a first cavity facing the second jaw, the second jaw may include a second cavity facing the first jaw, and when the biopsy device is in the closed configuration, the first cavity and the second cavity may form an enclosed volume. The biopsy device may include a protrusion having a sharp distal tip extending from a base of the first cavity toward the second jaw, and an opening disposed through an outer surface of the second jaw and in communication with the enclosed volume. The biopsy device may include a sharp rim extending from the second cavity toward the first jaw, the sharp rim extending at least partially around a circumference of the second cavity. The protrusion may be aligned with and/or received by the opening when the biopsy device is in the closed configuration. The second jaw may include a tang, and the biopsy device may include a clevis having a longitudinally-extending slot, a first pin configured to slide within the longitudinally-extending slot, a first link coupled to the tang of the second jaw at a first joint, the first link being configured to pivot about the first pin, and a pushing member configured to push the first pin within the longitudinally-extending slot. The pushing member may be configured to push the first pin from a first position in the longitudinally-extending slot when the biopsy device is in the closed configuration, distally to a second position in the longitudinally-extending slot to move the biopsy device to the open configuration. The biopsy device may include a second pin coupled to the second jaw, the second jaw being configured to pivot about the second pin, and the first link may be configured to pivot about the first pin in a first direction while the first pin is pushed distally by the pushing member, causing the second jaw to pivot about the second pin in a second direction that is opposite to the first direction. The first jaw may include a tang, and the biopsy device may include a second link coupled to the tang of the first jaw at a second joint, the second link being configured to pivot about the first pin, and the first jaw being configured to pivot about the second pin, and the second link may be configured to pivot about the first pin in the second direction while the first pin is pushed distally by the pushing member, causing the first jaw to pivot about the second pin in the first direction. The first jaw and the second jaw may both be movable relative to a longitudinal axis of the biopsy device. The first jaw may be fixed relative to a longitudinal axis of the biopsy device, and the second jaw may be movable relative to the longitudinal axis of the biopsy device. The first jaw may include a plurality of beveled surfaces that lead to the first distal tip, and the second jaw may include a plurality of beveled surfaces that lead to the second distal tip. The biopsy device may include one or more sharp teeth disposed on at least one of the first jaw and the second jaw.

In yet another example, the present disclosure is directed to a biopsy device that may include an elongate member extending from a proximal end to a distal end, the elongate member including a lumen extending from the proximal end toward the distal end, a tip at the distal end configured to pierce tissue, and at least one opening extending through a side surface of the elongate member, an actuating member extending from a proximal end toward a distal end, through the lumen of the elongate member, and at least one flexible band coupled to the distal end of the actuating member and to the distal end of the elongate member, the at least one flexible band being configured to transition between a radially-collapsed configuration and a radially-expanded configuration as the flexible band moves radially outward of the opening.

When the at least one flexible band is in the radially-collapsed configuration, distal movement of the actuating member may be configured to transition the at least one flexible band toward the radially-expanded configuration, and when the at least one flexible band is in the radially-expanded configuration, proximal movement of the actuating member may be configured to transition the at least one flexible band back toward the radially-collapsed configuration. When the at least one flexible band is in the radially-collapsed configuration, a portion of the at least one flexible band may be disposed within the lumen proximal to a proximal end of the at least one opening. The biopsy device may include an energy generator configured to deliver electrocautery or RF energy to the at least one flexible band, and the actuating member may be configured to deliver the electrocautery energy or the RF energy from the energy generator to the at least one flexible band.

In yet another example, the present disclosure is directed to a biopsy device that may include an outer elongate member extending from a proximal end to a distal end, the outer elongate member including a first lumen extending from the proximal end toward the distal end, an inner elongate member extending from a proximal end to a distal end, and through the first lumen of the outer elongate member, the inner elongate member including a second lumen, an actuating member extending from a proximal end to a distal end, through the second lumen of the inner elongate member, a tip configured to pierce tissue at the distal end of the actuating member, and at least one flexible band coupled to the distal end of the inner elongate member, and to the tip, the at least one flexible band being configured to transition between a radially-collapsed configuration and a radially-expanded configuration.

In yet another example, the present disclosure is directed to a biopsy device that may include a distal tip configured to pierce tissue, a movable arm proximal to the distal tip, the movable arm having a free proximal end and a distal end, the movable arm being configured to pivot relative to a longitudinal axis of the biopsy device about the distal end of the movable arm.

The biopsy device may include a link, and the movable arm may be configured to pivot relative to the longitudinal axis via movement of the link distally and pivoting of the link. The distal end of the movable arm may include a gear, and the biopsy device further may include an actuating member having a rack gear in communication with the gear of the movable arm. Proximal movement of the actuating member may cause the proximal end of the movable arm to extend radially away from the longitudinal axis, and distal movement of the actuating member may cause the proximal end of the movable arm to move toward the longitudinal axis.

In yet another example, the present disclosure is directed to a biopsy device that may include a first assembly having a support and a plurality of first tips extending distally from the support and configured to pierce tissue, the plurality of first tips being circumferentially spaced apart from one another, and a second assembly having an elongate member and a plurality of second tips extending distally from the elongate member and configured to pierce tissue, the plurality of second tips being circumferentially spaced apart from one another, wherein the first assembly and the second assembly are collinear, the elongate member of the second assembly extends through the support of the first assembly, and the first tips and the second tips alternate with one another about a central longitudinal axis of the biopsy device.

The biopsy device may include a drive coupled to at least one of the first assembly and the second assembly, the drive being configured to cause the first assembly and the second assembly to longitudinally oscillate relative to one another.

In yet another example, the present disclosure is directed to a biopsy device that may include a needle extending from a proximal end toward a distal end, the needle having a first lumen extending from the proximal end toward the distal end, and a piercing member extending through the first lumen and having a tip at a distal end of the piercing member configured to pierce tissue, the piercing member may include a second lumen extending through the piercing member, at least one opening disposed through an outer surface of the piercing member and in communication with the second lumen, and at least one expandable member extending from the outer surface of the piercing member adjacent to the at least one opening, the at least one expandable member being biased toward a radially-expanded configuration, wherein when the piercing member is disposed within the needle, the at least one expandable member is constrained by the needle in a radially-collapsed configuration, when the piercing member extends distally of the distal end of the needle, the at least one expandable member is configured to expand to the radially-expanded configuration, and rotation of the piercing member about a central longitudinal axis causes the at least one expandable member to collect tissue within the at least one opening.

BRIEF DESCRIPTION OF THE FIGURES

The accompanying drawings, which are incorporated in and constitute a part of this specification, illustrate various examples and together with the description, serve to explain the principles of the disclosed examples.

FIG. 1 is a side view of a biopsy device according to an example of the present disclosure.

FIGS. 2 and 3 are side cross-sectional views of a portion of the biopsy device of FIG. 1.

FIGS. 5 and 6 are schematic views of a biopsy device according to an example of the present disclosure.

FIGS. 9 and 9A are partial side cross-sectional views of a biopsy device according to another example of the present disclosure.

FIGS. 13, 13A, 14, 14A, 15, and 16 are partial side cross-sectional views of biopsy devices according to various examples of the present disclosure.

FIG. 18 is a side view of the biopsy device of FIG. 17.

FIG. 19 is a cross-sectional view of the biopsy device taken along line 19-19 of FIG. 18.

DETAILED DESCRIPTION

Figure 3:
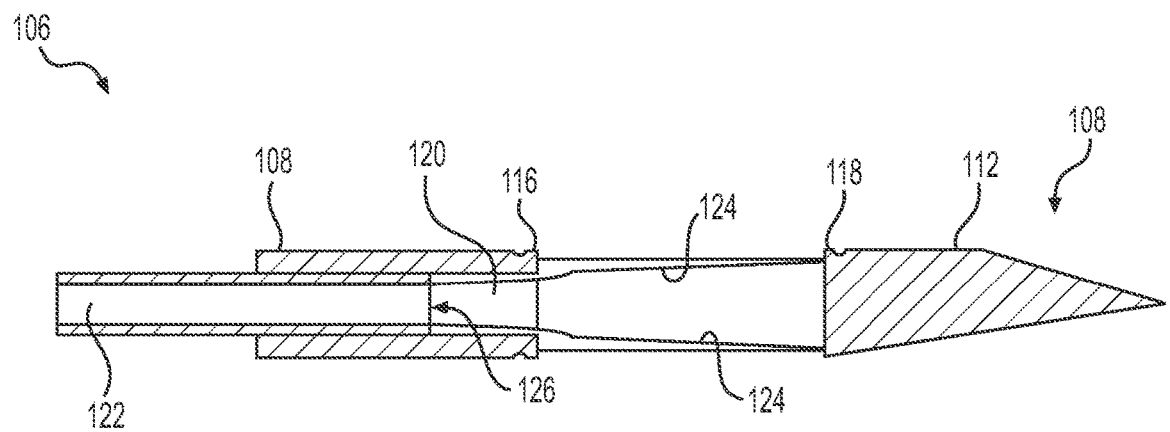

Reference will now be made in detail to examples of the present disclosure, which are illustrated in the accompanying drawings. Wherever possible, the same reference numbers will be used throughout the drawings to refer to the same or like parts.

Devices of the present disclosure may be inserted through a working channel of an elongate member such as, e.g., an endoscope, a ureteroscope, a colonoscope, a hysteroscope, a uteroscope, a bronchoscope, or a cystoscope, to reach tissue to be biopsied in a patient. In some examples, the tissue to be biopsied may be disposed radially outward of surface tissue defining the body lumen. Once a device is positioned at an appropriate target area, e.g., adjacent to the tissue to be collected, a physician may puncture the surface or wall surrounding a body lumen to access the tissue to be biopsied. Once the surface tissue has been penetrated, mechanisms may be deployed that allow the disclosed devices to acquire tissue samples.

A biopsy system 100 is shown in FIGS. 1-4. Biopsy system 100 may include an outer elongate member 102 extending from a proximal end (not shown) toward a distal end 104. The outer elongate member 102 may include a lumen 105 extending therethrough, which may receive a biopsy device 106. Biopsy device 106 may include a piercing shaft 108 extending from a proximal end (not shown) toward a distal end 110. A portion of biopsy device 106, including for example, the proximal end of biopsy device 106 may include a braided catheter 107. A piercing tip 112 may be disposed at distal end 110, and may be configured to pierce through various tissues. The piercing tip 112 may have any suitable piercing or needle tip shapes and/or geometries, such as, e.g., a single bevel, multiple bevels, conical, Sprotte, diamond, Franseen, Tuohy, or the like.

Figure 4:
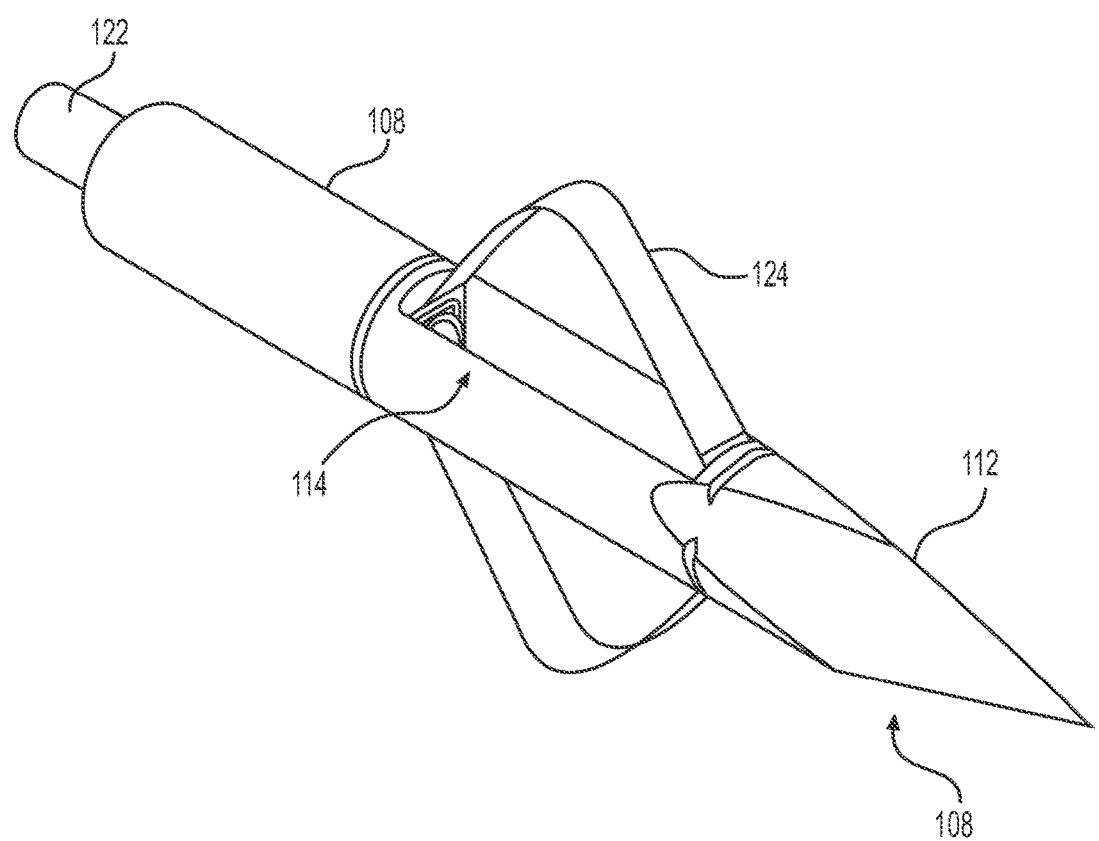
FIG. 4 is a perspective view of a portion of the biopsy device of FIG. 1.

Piercing shaft 108 may include one or more openings 114 that extend through a circumferential side surface of piercing shaft 108. As shown in FIGS. 2 and 4, piercing shaft 108 includes two openings 114 that are on opposing circumferential sides of piercing shaft 108. It is further contemplated that piercing shaft 108 may include only one opening, or may include additional openings spaced circumferentially from one another (e.g., three, four, or more) at evenly or unevenly spaced intervals. The openings 114 may be proximal to the piercing tip 112, and may extend from a first end 116 to a second end 118. The first end 116 may be disposed closer to the proximal end of piercing shaft 108 than second end 118, while the second end 118 may be disposed closer to the distal end 110 of piercing shaft 108 than first end 116. Piercing shaft 108 also may include markers 119, such as, e.g., echogenic markers, proximal and distal to openings 114 to help visualize the piercing shaft 108 (and particularly first ends 116 and second ends 118 of the openings 114) during a biopsy procedure. This may assist in properly positioning openings 114 at the location of the tissue to be biopsied.

Piercing shaft 108 may include a lumen 120 that extends from its proximal end toward distal end 110. Biopsy device 106 also may include a push rod 122 that extends and slides within lumen 120. One or more bands 124 may be coupled to both a distal end 126 of push rod 122, and to the distal end 110 of piercing shaft 108. In one example, the one or more bands 124 may be coupled to a proximal portion of piercing tip 112. The bands 124 may be reciprocally movable between a radially-collapsed configuration (FIG. 3) and a radially-expanded configuration (FIG. 2) via actuation of push rod 122. For example, as shown in FIG. 3, in the radially-collapsed configuration, the distal end 126 of push rod 122 and the one or more bands 124 may be disposed within lumen 120. In this radially-collapsed configuration, distal end 126 of push rod 122 also may be disposed proximally of first end 116 of opening 114. At least a portion of each of the one or more bands 124 also may be disposed within lumen 120 proximal to first end 116. Push rod 122 may be advanced distally relative to a stationary piercing shaft 108 (or piercing shaft 108 may be pulled proximally relative to push rod 122 while push rod 122 is held stationary) to cause the one or more bands 124 to move from the radially-collapsed configuration of FIG. 3 to the radially-expanded configuration of FIG. 2.

The one or more bands 124 may include any suitable material, such as, e.g., stainless steel, a shape memory material (nitinol, elgiloy or the like), or another suitable material. In certain examples where band 124 includes a shape memory material, band 124 may be prebent into either the collapsed or expanded configurations. In one example, band 124 may be any suitable wire capable of cutting tissue. For example, band 124 may include sharp outer edges. In some examples, band 124 may have any cross-sectional geometry including, but not limited to, square, flat, rectangular, round, semi-circular, and triangular. Furthermore, the cross-sectional geometry of band 124 may vary along its length. In another example, band 124 may be configured for electrocauterization procedures. For example, band 124 may conduct electricity. Electrocauterization is the process of damaging or destroying tissue using heat generated by passing an electric current through a conductive probe or wire. That procedure may be used for cutting through soft tissue. In various examples of the present disclosure, band 124 may be adapted to carry sufficient current to generate the heat required for electrocautery. Furthermore, band 124 may be able to withstand repeated heat cycling without developing hot spots and subsequently breaking down. In some examples, band 124 may include insulation along any portion or portions. Band 124 may be a single strand of wire, formed as solid or braided material. In addition to being configured to carry and deliver electrical energy to tissue, other energy sources may be utilized. For example, radio frequency (RF) energy may be applied though band 124.

Referring to FIGS. 5 and 6, the one or more bands 124 may be coupled to an energy generator 150 via push rod 122 and/or an electrically conductive member 152. Thus, in some examples, push rod 122 may include an electrically conductive material configured to transmit energy from energy generator 150 to the one or more bands 124. Energy generator 150 may be any suitable generator known in the art for delivering electrical and/or RF energy. It is also contemplated that push rod 122, electrically conductive member 152, and the one or more bands 124 may be electrically insulated from other portions of biopsy system 100, including, but not limited to, puncture shaft 108, piercing tip 112, elongate member 102, and handle 140. However, in some examples, piercing tip 112 may be coupled to energy generator 150 or another suitable source of energy to help piercing tip 112 pierce through tissue via energy delivery.

In another example, the band 124 may be a substantially hollow wire having one or more holes (not shown) disposed on its surface. This arrangement may facilitate additional capabilities, such as irrigation, aspiration, medication delivery, or lubrication, before, during, or after the cutting process. Band 124 may also comprise abrasive coatings or projections, such as barbs, saw, or blades, although such protrusions may be sized to allow movement of the bands 124 through openings 114.

FIGS. 5 and 6 also show a handle 140 having a housing 142, a subassembly 144, and an actuator 146. Subassembly 144 may be coupled to a proximal end of push rod 122, and may move longitudinally within housing 142 to transition biopsy device 100 from the radially-collapsed configuration to the radially-expanded configuration. One or more locking features 148 may be disposed on an outer surface of subassembly 144, and may be configured to interact with corresponding locking features 151 on an inner surface of housing 142. The interaction of locking features 148 and 151 may maintain subassembly 144 in a distal portion of housing 142, which may help keep biopsy device 106 in the radially-expanded configuration. Subassembly 144 also may be configured to rotate biopsy device 106 in order to allow the one or more bands 124 to slice through tissue.

Actuator 146 may be configured to transfer the necessary rotational force to subassembly 144 and biopsy device 106. Actuator 146 may be a mechanical mechanism, such as, e.g., a rotatable dial, or may be an electrically powered motor, for example. Other handles and actuation mechanisms are also contemplated, including, e.g., manually-operated handles and mechanisms that cause the longitudinal and rotational movement of the bands 124.

One or more portions of biopsy system 100, including, e.g., elongate member 102, puncture shaft 108, piercing tip 112, among others, may include a lubricious coating. Lubricious coatings include both hydrophilic and non-hydrophilic polymer materials. In one example, the lubricious coating may be a hydrogel.

Figure 7:
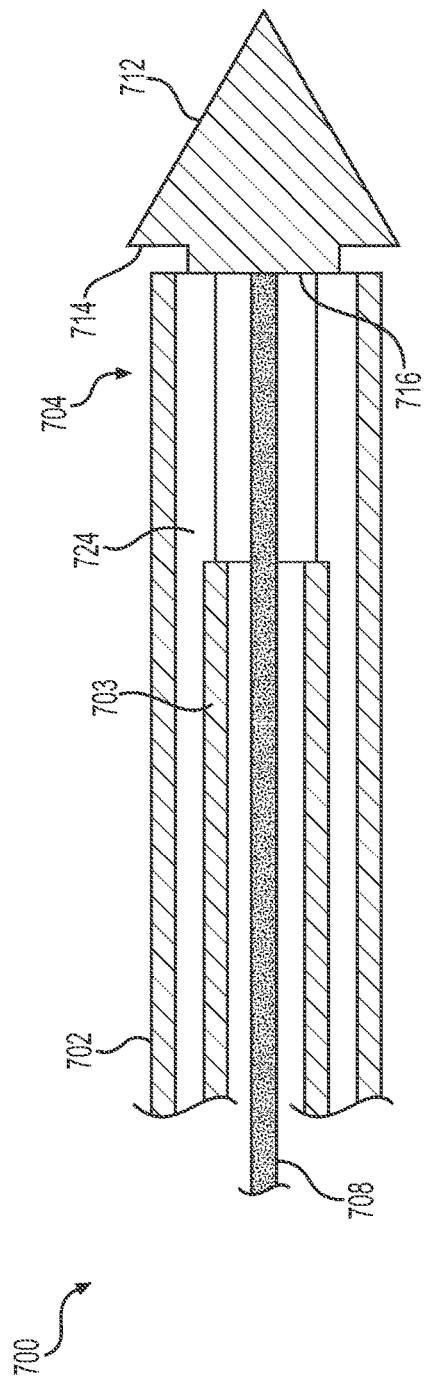
FIGS. 7 and 8 are partial side cross-sectional views of a biopsy device according to another example of the present disclosure.

A biopsy device 700 is shown in FIG. 7, and may include an outer elongate member 702 that extends from a proximal end (not shown) toward a distal end 704. A lumen may extend through outer elongate member 702 (which may be tubular) from its proximal end toward distal end 704. In some examples, outer elongate member 702 may be substantially rigid and may be formed from e.g., stainless steel or a shape memory material. In other examples, outer elongate member 702 may be substantially flexible. An inner elongate member 703 (which also may be tubular) may extend through the lumen of outer elongate member 702. Inner elongate member 703 may be substantially similar to outer elongate member 702, but may have smaller dimensions (e.g., inner elongate member 703 may have a smaller diameter than outer elongate member 702).

Figure 8:
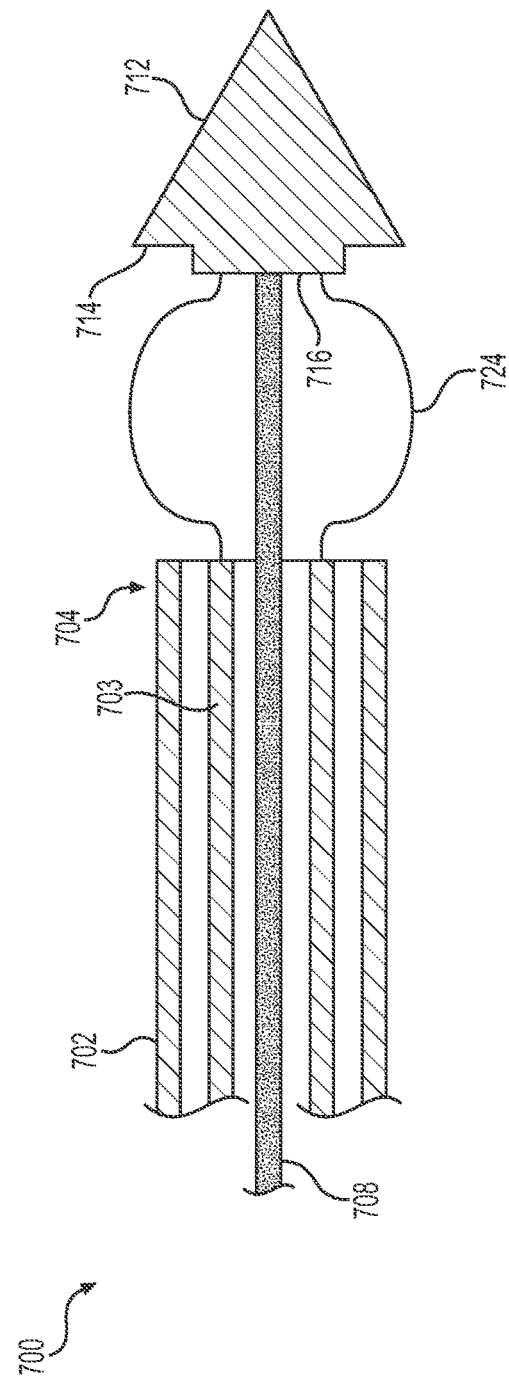

A rod 708 may extend through a lumen of inner elongate member 703, and a piercing tip 712 may be disposed at the distal end of rod 708. In some examples, a wire, cable, or other suitable member may be used instead of rod 708. Rod 708 and piercing tip 712 may include one or more of the same features as push rod 122 and piercing tip 112, respectively, as set forth above. Additionally, piercing tip 712 may include a proximally-facing surface 716, which, in at least some examples, may be the proximalmost surface of piercing tip 712. Piercing tip 712 also may include at least one stepped portion 714 that is longitudinally offset distally from the proximally-facing surface 716. The stepped portion 714 may receive and/or otherwise cooperate with distal end 704 of the outer elongate member 702. In some examples, stepped portion 714 and distal end 704 of outer elongate member 702 may be magnetically attracted to one another in order to help maintain contact between the outer elongate member 702 and the stepped portion 714 (which may be ring-shaped) in the closed configuration of biopsy device 700. One or more bands 724 may be coupled to the distal end of inner elongate member 703, and to a proximal end of piercing tip 712 (e.g., to proximally-facing surface 716). The one or more bands 724 may be substantially similar to the one or more bands 124 described above. In examples where the one or more bands 724 are prebent or otherwise biased into an open, radially-expanded configuration (as shown in FIG. 8), the magnetic attraction between the distal end 704 of outer elongate member 702 and stepped portion 714 of piercing tip 712 may help maintain biopsy device 700 in the closed configuration.

While in the closed configuration shown in FIG. 7, elongate member 702 may be withdrawn proximally to expose the one or more bands 724. Once elongate member 702 is pulled proximally, rod 708 also may be pulled proximally while the distal end of inner elongate member 703 remains stationary, causing the one or more bands 724 to move radially outward to the radially-expanded configuration of FIG. 8.

Biopsy device 700 may be configured to deliver electrocautery, RF, or another suitable energy to tissue. In one example, push rod 708 may be coupled at its proximal end to an energy source, such as, energy generator 150 set forth above. Energy generator 150 may deliver energy through push rod 708 and piercing tip 712 to the one or more bands 724. In another example, piercing tip 712 may not be electrically conductive, and energy may travel from push rod 708 to the one or more bands 724 via one or more electrically conductive wires (not shown). In yet another example, inner elongate member 703 may be conductive, and may deliver energy to the one or more bands 724. Outer elongate member 702 may be electrically insulated from any conductive members of biopsy device 700.

A physician may collect a sample disposed radially outward of a surface that defines a body lumen with either biopsy device 106 or biopsy device 700 by piercing the surface via a respective piercing tip, while the biopsy device is in the closed configuration. Then, the respective biopsy device may be transitioned from the closed configuration to the expanded configuration by an actuating mechanism, such as, e.g., handle 140 described with reference to FIGS. 5 and 6. Once the one or more bands are radially expanded, they may be rotated to pierce through the tissue to be collected. Once the tissue has been cut, the biopsy device may be repositioned to place bands 124 radially outward of the severed tissue, after which bands 124 may be transitioned back to the radially collapsed configuration, trapping removed tissue within the device. As set forth above, the piercing and/or cutting steps may be supplemented by a simultaneous energy delivery from an energy generator to assist with the piercing and/or cutting.

Figure 10:
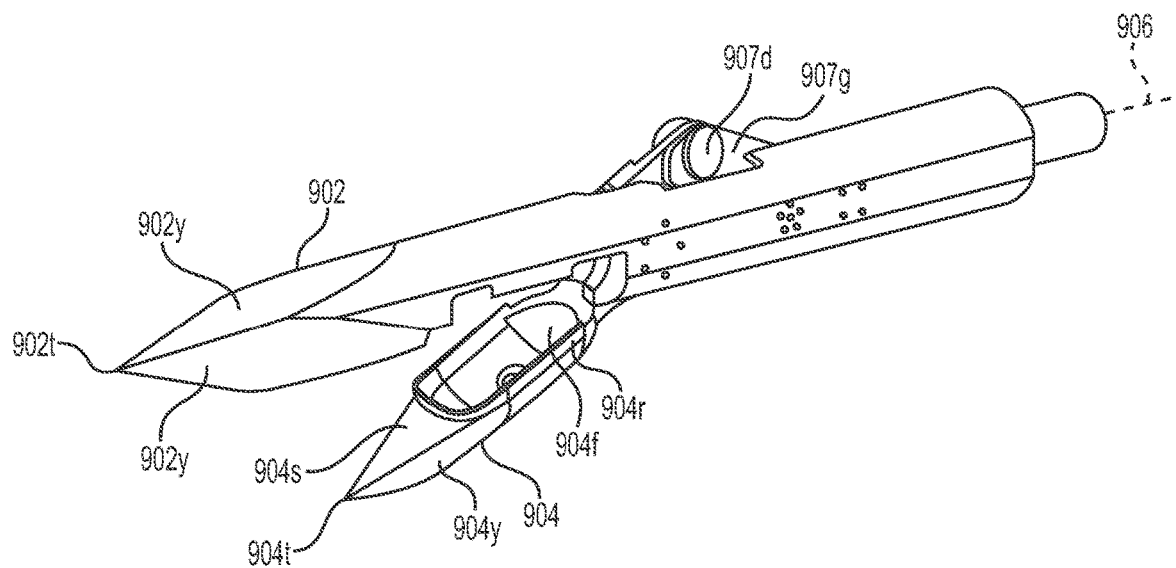
FIG. 10 is a perspective view of the biopsy device of FIGS. 9 and 9A.

A biopsy device 900 is shown in FIGS. 9, 9A, and 10. Biopsy device 900 may be a biopsy forceps having jaws 902 and 904. In this example, both jaws 902 and 904 may include a sharpened distal end. A piercing tip 908 may be at the distal end of jaw 902. Jaw 902 may include a plurality of beveled surfaces 902y that lead to a sharp distal tip 902t. In one example, at least three beveled surfaces 902y may form sharpened distal tip 902t, although other suitable numbers of surfaces are also contemplated. A cavity 902f may be formed in a radially-inward facing surface of jaw 902, and a protrusion 902g may be disposed within the cavity 902f. The protrusion 902g may have any suitable shape, e.g., conical, pyramidal, or the like, with a sharp tip extending toward a longitudinal axis 906 and toward jaw 904.

Jaw 904 also may include a plurality of beveled surfaces 904y and 904s that lead to a sharp distal tip 904t. In some examples, each of the beveled surfaces 902y of jaw 902 may have a larger surface area than each of the beveled surfaces 904s and 904y of jaw 904. Jaw 904 may include a cavity 904f disposed on a radially-inward facing side. The entirety of cavity 904f may be disposed proximal to the flat beveled surface 904s. Jaw 904 also may include an opening 904z in communication with cavity 904, which may allow fluid within cavity 904f to escape during tissue acquisition. The opening 904z may help biopsy device 900 obtain larger volumes of tissue during biopsy procedures by allowing fluid to escape. Protrusion 902g may align with and be received by opening 904z.

Referring to FIG. 9A, cavities 902f and 904f may form a partially-enclosed volume 915 (with the exception of the opening 904z) when biopsy device 900 is in the closed configuration. The distal end of jaw 902 includes a piercing tip 908 when biopsy device 900 is in the closed configuration. In at least one example, piercing tip comprises only jaw 902 as jaw 904 may be received entirely within the body of biopsy device 900 in the closed configuration. Thus, when device 900 is viewed from a point along longitudinal axis 906 distal to biopsy device 900, jaw 904 may be substantially or completely concealed by jaw 902, and hidden from view. Tip 904*t* is not within that view, as a portion of jaw 902 conceals tip 904*t*. This configuration may help reduce forces acting in the proximal direction when the piercing tip 908 is moved distally through tissue, and may help reduce the risk that the jaw 904 is unintentionally forced into the open configuration when closed, and the device 900 is moving distally through tissue. The piercing tip 908 may have any suitable piercing or needle tip shape, such as, e.g., a single bevel, multiple bevels, conical, Sprotte, diamond, Franseen, Tuohy, or the like.

Jaw 902 may be fixed, and jaw 904 may be movable relative to jaw 902 via any suitable actuation mechanism. In the example shown, the actuation mechanism includes a push/pull member 905 movable relative to a clevis 907*c*. Clevis 907*c* may include a longitudinally extending slot 907*e* that slidably receives a pin 907*a*. A link 907 may be coupled to pin 907*a*, and may be configured to rotate about the sliding pin 907*a*. Link 907 may be coupled to a tang 904*a* of jaw 904 at a joint 907*d*, and jaw 904 may longitudinally fixed to a remainder of biopsy device 900 by a pin 907*b*. Jaw 904 also may be configured to pivot and rotate about the pin 907*b*. A slot 907*g* may be disposed in an upper portion of clevis 907*c*, and through which link 907, joint 907*d*, and tang 904*a* may move. When in the closed configuration shown in FIG. 9A, push/pull member 905 may be pushed distally, causing pin 907*a* to move distally within the slot 907*e*. The distal movement of push/pull member 905 also may cause link 907 to pivot in a first direction about pin 907*a*, while jaw 904 pivots about link 907*b* in a second direction opposite to the first direction, thereby moving biopsy device 900 into the open configuration of FIGS. 9 and 10. Push/pull member 905 may be retracted proximally to return biopsy device 900 to the closed configuration (or a partially-closed configuration if captured tissue prevents the jaw 904 from returning to a fully-closed configuration). Jaws 902 and 904 may open and close by any other suitable mechanisms.

To biopsy tissue disposed radially outward of a body lumen with biopsy device 900, piercing tip 908 may be extended, while biopsy device 900 is in the closed configuration, distally through tissue surrounding the body lumen until jaws 902 and 904 are adjacent or in contact with tissue to be sampled. Once the jaws 902 and 904 are close to the target tissue, push/pull member 905 may be extended distally to open jaws 902 and 904. Once opened, jaws 902 and 904 may be pushed forward (distally) to place tissue within jaws 902 and 904, and then jaws 902 and 904 may be used to clamp down on the target tissue. If necessary, jaws 902 and 904 then may be rotated, twisted, or pulled, to tear the clamped tissue. Alternatively, a sharp rim 904*r* that extends from cavity 904*f* towards jaw 902 may be used to sever the target tissue. Rim 904*r* may extend at least partially about the circumference of cavity 904*f*, and may be raised above surface 904*s*. The presence of protrusion 902*g* on jaw 902 may help ensure that at least some of the severed tissue remains captured by the jaws 902 and 904. In alternative embodiments, tissue may be severed in vivo by using sharp distal edges of jaws 902 or 904 formed at the intersection of the beveled surfaces. In such examples, the jaws 902 and 904 may be used to cut or scrape tissue, and then jaws 902 and 904 may be closed around the severed sample.

Figure 11:
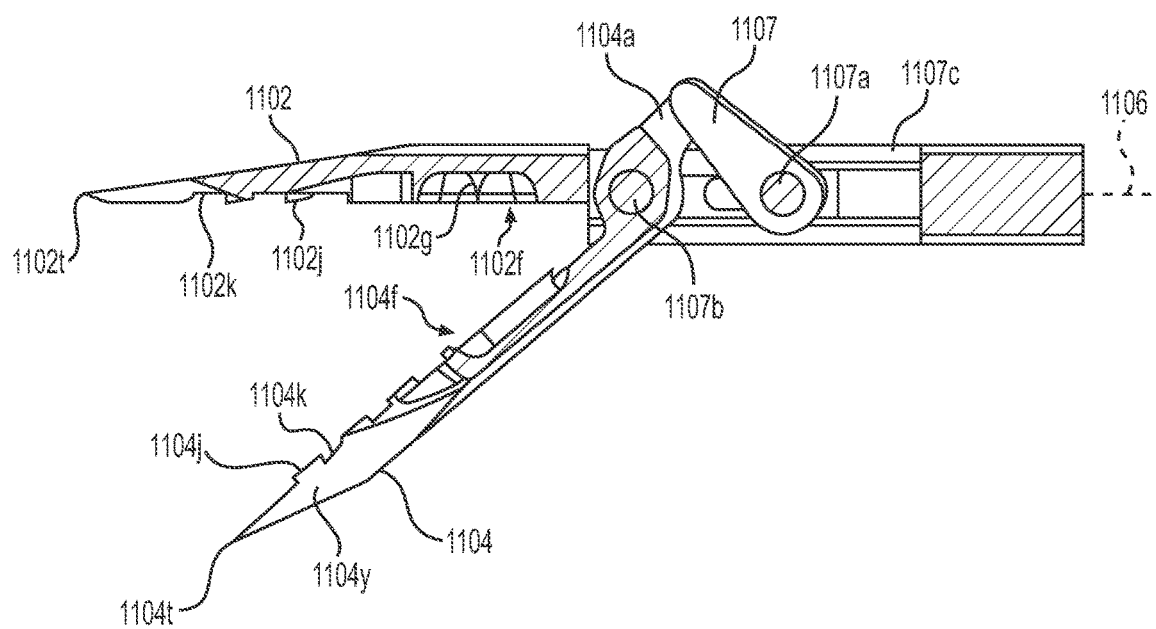
FIGS. 11 and 11A are partial side cross-sectional views of a biopsy device according to another example of the present disclosure.
Figure 11A:
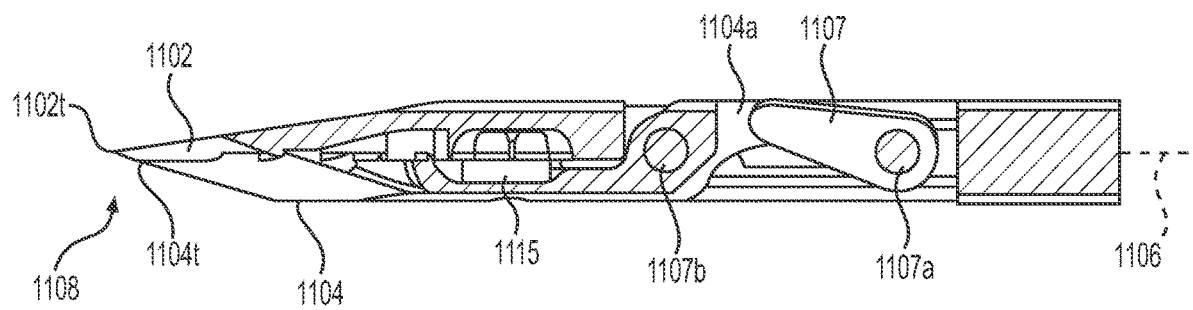
Figure 12:
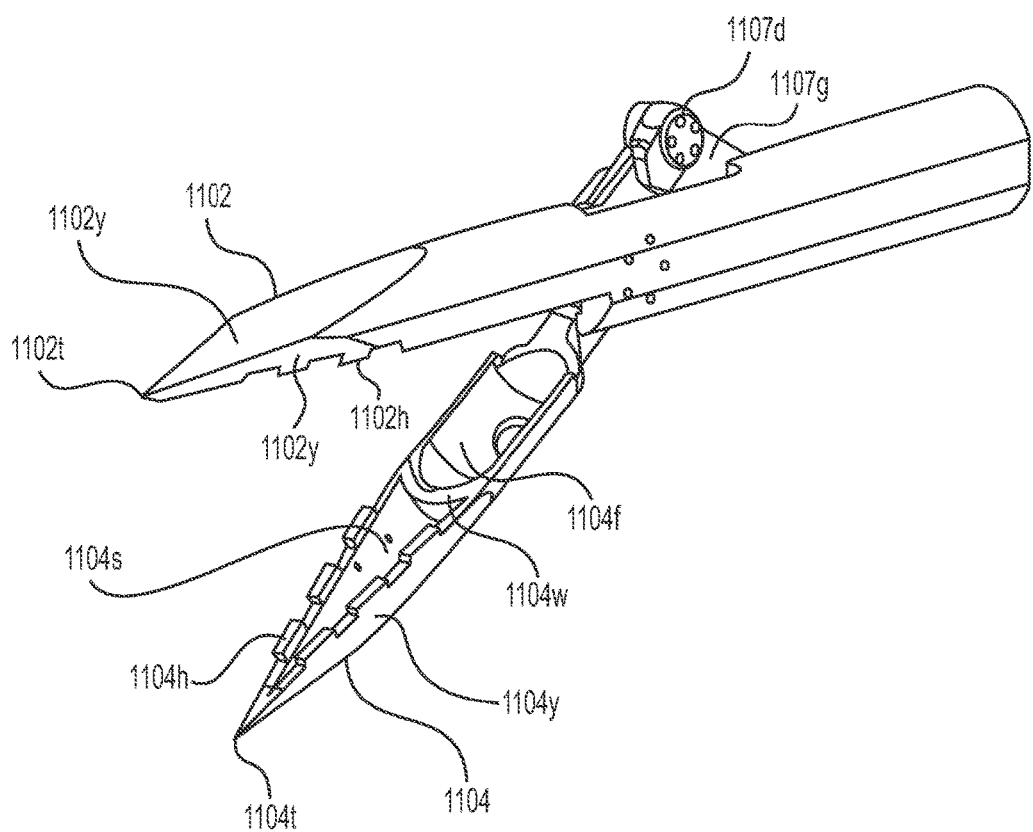
FIG. 12 is a perspective view of the biopsy device of FIGS. 11 and 11A.

A biopsy device 1100 is shown in FIGS. 11, 11A, and 12. Biopsy device 1100 may be a biopsy forceps having jaws 1102 and 1104. In this example, both jaws 1102 and 1004 may include a sharpened distal end. A piercing tip 1108 (shown in FIG. 11A) may be formed by the distal ends of jaws 1102 and 1104. Jaw 1102 may include a plurality of beveled surfaces 1102*y* that lead to a sharp distal tip 1102*t*. In one example, at least two beveled surfaces 1102*y* may form sharpened distal tip 1102*t*, although other suitable numbers of surfaces are also contemplated. A cavity 1102*f* may be formed in a radially-inward facing surface of jaw 1102, and a protrusion 1102*g* substantially similar to protrusion 902*g* may be disposed within the cavity 1102*f*.

Jaw 1104 also may include a plurality of beveled surfaces 1104*y* that lead to a sharp distal tip 1104*t*. Jaw 1104 may include a cavity 1104*f* disposed on a radially-inward facing side. The entirety of cavity 1104*f* may be disposed proximal to another cavity 1104*s*. Jaw 1104 also may include an opening 1104*z* in communication with cavity 1104*f*, which may allow fluid within cavity 1104*f* to escape during tissue acquisition. The opening 1104*z* may help biopsy device 1100 obtain larger volumes of tissue during biopsy procedures by allowing fluid to escape.

Referring to FIG. 11A, cavities 1102*f* and 1104*f* may form a partially-enclosed volume 1115 (with the exception of the opening 1104*z*) when biopsy device 1100 is in the closed configuration. The distal ends of jaws 1102 and 1104 may form a piercing tip 1108 when biopsy device 1100 is in the closed configuration. Thus, when viewed from a point along longitudinal axis 1106 distal to biopsy device 1100, a portion of both jaws 1102 and 1104 may be visible such that neither jaw completely conceals the other jaw in the piercing direction.

While both jaws 1102 and 1104 may form the piercing tip 1108, it is contemplated that only one of sharp distal tips 1102*t* and 1104*t* form the distalmost portion of piercing tip 1108. As shown, distal tip 1102*t* of the immobile jaw is the distalmost portion of piercing tip 1108, although distal tip 1104*t* of the movable jaw 1104 could be the distalmost portion in another example. The cavity 1104*s* of movable jaw 1104 may be configured to receive one or more of the beveled surfaces 1102*y*. Thus, in the closed configuration, the contours of piercing tip 1108 may include portions where beveled surfaces of jaws 1102 and 1104 overlap with one another, and other portions are formed by the beveled surface of only one of the jaws 1102 and 1104. The piercing tip 1108 may have any suitable piercing or needle tip shape, such as, e.g., a single bevel, multiple bevels, conical, Sprotte, diamond, Franseen, Tuohy, or the like.

Jaw 1102 may be fixed, and jaw 1104 may be movable relative to jaw 1102 via any suitable actuation mechanism. In the example shown, the actuation mechanism for jaws 1102 and 1104 may be substantially similar to those discussed with respect to biopsy device 900. Thus, push/pull member 1105, clevis 1107*c*, slot 1107*e*, pin 1107*a*, link 1107, tang 1104*a*, joint 1107*d*, slot 1107*g*, and pin 1107*b* may be shaped in a substantially similar manner, and function in a substantially similar manner as push/pull member 905, clevis 907*c*, slot 907*e*, pin 907*a*, link 907, tang 904*a*, joint 907*d*, slot 1107*g*, and pin 907*b*, as set forth above. Tissue also may be sampled or biopsied in a substantially similar manner as set forth above with respect to biopsy device 900. Alternatively, teeth 1102*h* and 1104*h* may be used to clamp, pierce, or cut through the tissue.

A biopsy device 1300 is shown in FIGS. 13 and 13A. Biopsy device 1300 may be substantially similar to biopsy device 1100 described above, except that both jaws 1302 and 1304 may be movable and pivot relative to a longitudinal axis 1306. Thus, jaw 1302, distal tip 1302t, beveled surfaces 1302y, cavity 1302f, protrusion 1302g, jaw 1304, distal tip 1304t, cavity 1304f, and volume 1315 may be substantially similar to jaw 1102, distal tip 1102t, beveled surfaces 1102y, cavity 1102f, protrusion 1102g, jaw 1104, distal tip 1104t, cavity 1104f, and volume 1115 described with reference to FIG. 11 above, except that jaw 1302 may also include a tang 1302a.

In the example shown, the actuation mechanism includes a push/pull member 1305 movable relative to a clevis 1307c. Clevis 1307c may include a longitudinally extending slot 1307e that slidably receives a pin 1307a. Links 1307 and 1310 may be coupled to pin 1307a, and may be configured to rotate about the sliding pin 1307a. Link 1307 may be coupled to a tang 1304a of jaw 1304 at a joint 1307d, and jaw 1304 may longitudinally fixed to a remainder of biopsy device 1300 by a pin 1308. Jaw 1304 also may be configured to pivot and rotate about the pin 1308. Link 1310 may be coupled to tang 1302a of jaw 1302 at a joint 1310d, and jaw 1302 also may longitudinally fixed to a remainder of biopsy device 1300 by pin 1308. Jaw 1302 also may be configured to pivot and rotate about the pin 1308. When in the closed configuration shown in FIG. 13A, push/pull member 1305 may be pushed distally, causing pin 1307a to move distally within the slot 1307e. The distal movement of push/pull member 1305 also may cause link 1307 to pivot in a first direction about pin 1307a, while jaw 1304 pivots about pin 1308 in a second direction opposite to the first direction. The distal movement of push/pull member 1305 also may cause link 1310 to pivot in the second direction about pin 1307a, while jaw 1302 pivots in the first direction about pin 1308, thereby moving biopsy device 1300 into the open configuration of FIG. 13. Push/pull member 1305 may be retracted proximally to return biopsy device 1300 to the closed configuration (or a partially-closed configuration if captured tissue prevents the jaws 1302 and 1304 from returning to a fully-closed configuration). Tissue also may be sampled or biopsied in a substantially similar manner as set forth above with respect to biopsy devices 900 and 1100.

Figure 14:
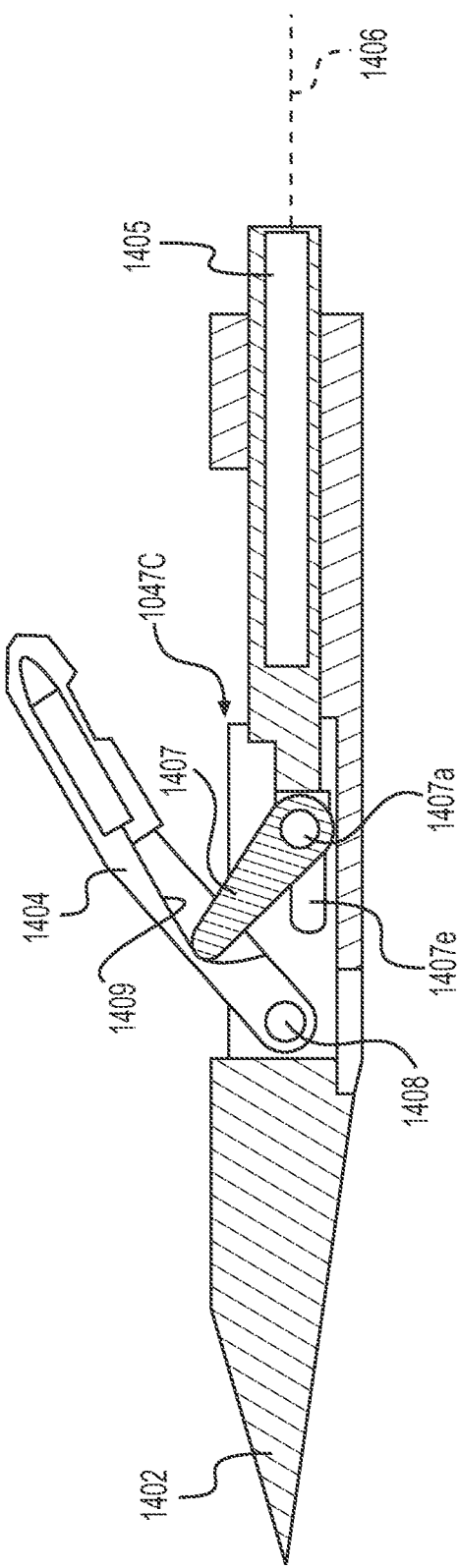

A biopsy device 1400 is shown in FIG. 14. Biopsy device 1400 may include a piercing tip 1402, and a movable arm 1404 disposed proximal to piercing tip 1402. The movable arm 1404 may be movable relative to piercing tip 1402 via any suitable actuation mechanism, such as, a push/pull member 1405 movable relative to a clevis 1407c. Clevis 1407c may include a longitudinally extending slot 1407e that slidably receives a pin 1407a. A link 1407 may be coupled to pin 1407a, and may be configured to rotate about the sliding pin 1407a. A distal end of link 1407 may be received within and fixed to a groove 1409 of arm 1404. Arm 1404 may be longitudinally fixed to a remainder of biopsy device 1400 by a pin 1408. Arm 1404 also may be configured to pivot and rotate about the pin 1408. When in a closed configuration shown in FIG. 14A, push/pull member 1405 may be pushed distally, causing pin 1407a to move distally within the slot 1407e. The distal movement of push/pull member 1405 also may cause link 1407 to pivot in a first direction about pin 1407a, pushing arm 1404 to pivot about link 1408 in a second direction opposite to the first direction, thereby moving biopsy device 1400 into the open configuration of FIG. 14. Push/pull member 1405 may be retracted proximally to return biopsy device 1400 to the closed configuration (or a partially-closed configuration if captured tissue prevents the arm 1404 from returning to a fully-closed configuration).

Figure 14A:
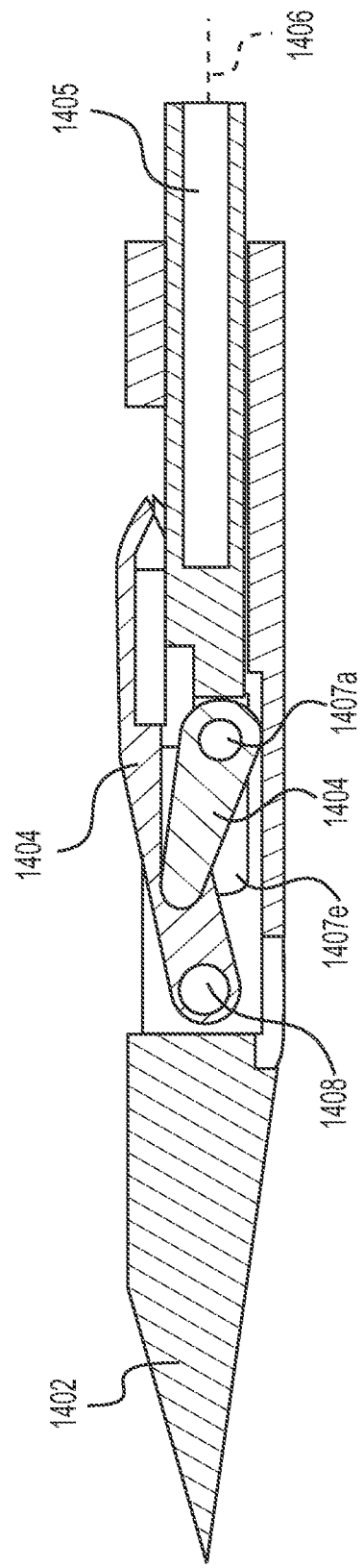

In the radially-collapsed configuration of biopsy device 1400 shown in FIG. 14A, movable arm 1404 may be substantially parallel to a longitudinal axis 1406. In a radially-expanded configuration shown in FIG. 14, arm 1404 may be disposed in a position where the proximal end of movable arm 1404 is spaced apart from the longitudinal axis 1406 of biopsy device 1400. Thus, movable arm 1404 may be fixed to the body of biopsy device 1400 at its distal end, and may pivot about its distal end.

To biopsy tissue disposed radially outward of a body lumen with biopsy device 1400, piercing tip 1402 may be extended, while biopsy device 1400 is in the closed configuration, distally through tissue surrounding the body lumen until arm 1404 is adjacent or in contact with tissue to be sampled. Then, push/pull member 1405 may be extended distally to move arm 1404 to the radially-expanded configuration of FIG. 14. In certain exemplary methods, the entire device 1400 may then be pulled proximally to place tissue between arm 1404 and a portion of device 1400. Then, arm 1404 may be used to clamp down on a target tissue, after which, the biopsy device 1400 may be rotated, twisted, or pulled, to tear the targeted tissue. In alternative embodiments, tissue may be severed by sharp teeth or a rimmed surface of arm 1404 or by using sharp distal edges of piercing tip 1402 formed at the intersection of the beveled surfaces, or may be severed in another suitable manner prior to moving arm 1404 into the radially-expanded configuration. In such examples, arm 1404 may be used to clamp down and capture tissue that has already been severed.

Figure 15:
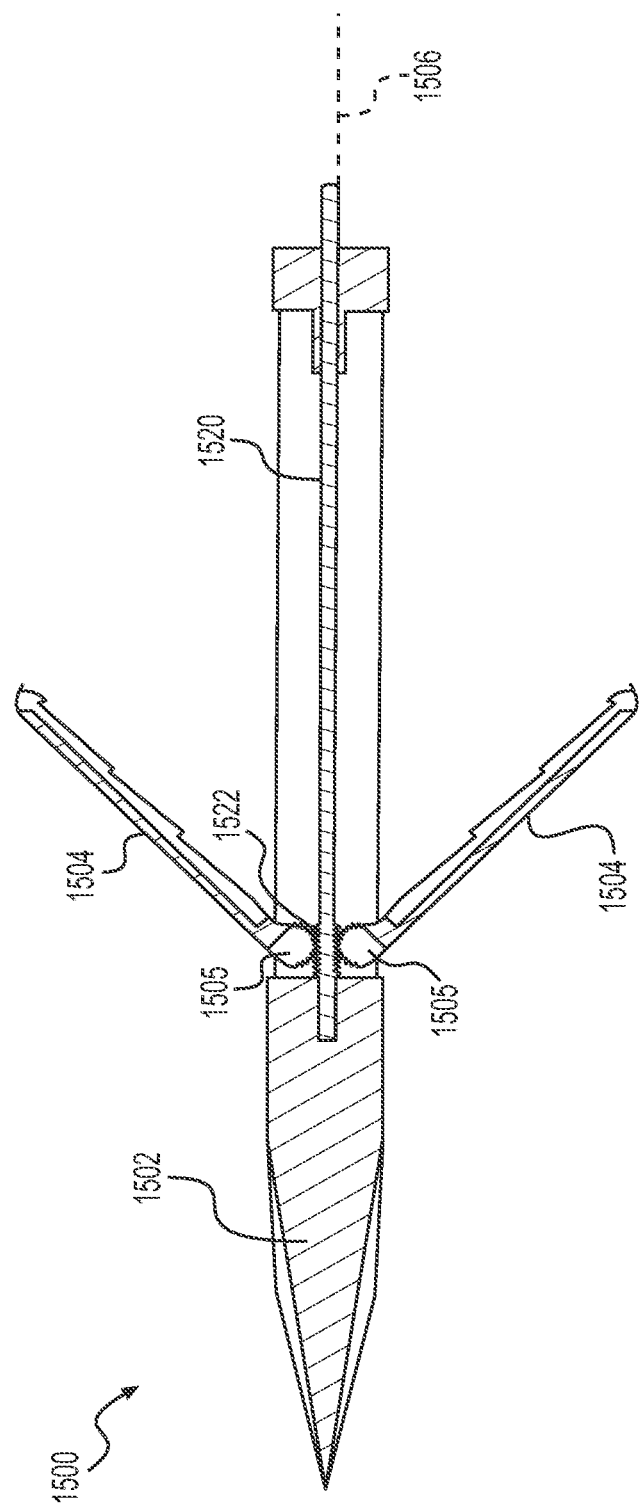

A biopsy device 1500 is shown in FIG. 15. Biopsy device 1500 may include a piercing tip 1502, and movable arms 1504 disposed proximal to piercing tip 1502. Each movable arm may include a gear 1505 disposed at its distal end. The movable arms 1504 may be movable relative to a longitudinal axis 1506 via a push/pull member 1520 having one or more gear racks 1522 configured to engage with one or more of the gears 1505. As shown in FIG. 15, push/pull member 1520 includes two gear racks 1522 disposed on opposing sides, which are able to actuate two movable arms 1504 simultaneously. In the example of FIG. 15, each movable arm 1504 may pivot relative to longitudinal axis 1506 to transition between a radially-collapsed configuration (not shown) and a radially-expanded configuration (shown in FIG. 15). In the radially-collapsed configuration, movable arms 1504 may be substantially parallel to the longitudinal axis 1506. To transition from the radially-collapsed configuration to the radially-expanded configuration, push/pull member 1520 may be pulled proximally. This proximal movement may cause gears 1522 and 1505 to interact and cause movable arms 1504 to pivot about their distal ends, while their proximal ends move radially outward to a position where the proximal ends of movable arms 1504 are spaced apart from the longitudinal axis 1506 of biopsy device 1500. In an alternative example, instead of gear racks 1522, push/pull member 1522 may include a spiral shaped gear that wraps around its outer surface, and that engages with gears 1505 of arms 1504. Tissue may be biopsied with biopsy device 1500 by positioning an opened arm 1504 distally of tissue to be collected, and retracting biopsy device 1500 proximally to position the tissue radially between the arm 1504 and the body of biopsy device 1500. Then, arms 1504 may be clamped down on the tissue to secure it. Once the targeted tissue is clamped, the tissue may be subsequently severed by pulling or rotating biopsy device 1500.

Or, sharp edges, rims, or teeth on the arms 1504 may sever tissue. Alternatively, arms 1504 may be clamped onto tissue that has already been severed. In one alternative example, biopsy device 1500 may include longitudinally staggered arms 1504 that are actuated by the same gear rack 1520. Thus, as a single gear rack 1520 of push/pull member 1522 is moved proximally, it may cooperate with the longitudinally staggered gears at different times. With such an example, biopsy device 1500 may be used to capture tissue in different locations by opening and closing the longitudinally staggered arms at different times.

Figure 16:
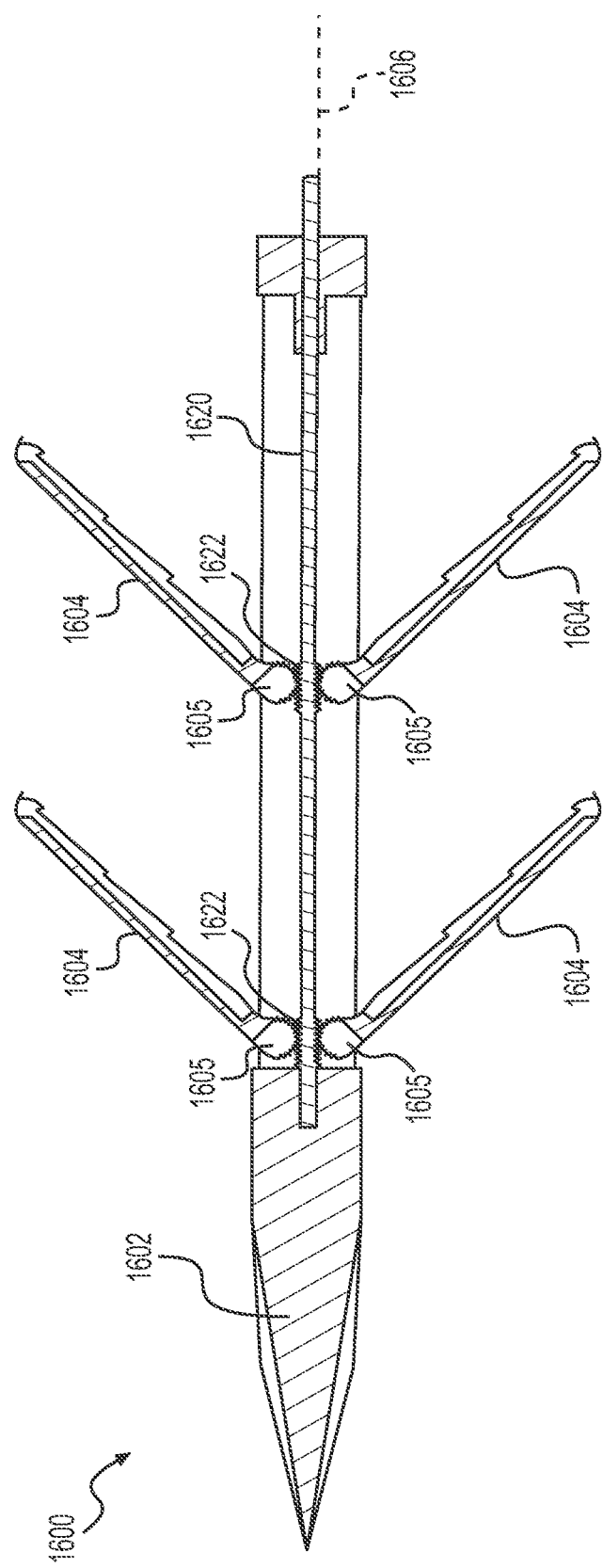

A biopsy device 1600 is shown in FIG. 16 that is substantially similar to biopsy device 1600, except that push/pull member 1620 may include a plurality of gear racks 1622 that are longitudinally spaced from one another along a push/pull member 1620. The gear racks 1622 may be configured to engage longitudinally spaced pairs of movable arms 1604 via gears 1605. In the example shown, biopsy device 1600 may be configured to actuate longitudinally spaced arms 1604 at the same time via the placement of multiple longitudinally spaced apart gear racks 1620. However, in alternative embodiments not pictured, push/pull member 1620 may actuate the longitudinally spaced arms 1604 at separate times via one or more gear racks 1620, or by one or more other gear-type mechanisms. Thus, biopsy device 1600 may be used to capture tissue in different locations by opening and closing the longitudinally staggered arms at different times. Movable arms 1604 may otherwise clamp and secure tissue in a substantially similar manner as set forth above with respect to movable arms 1504.

Figure 17:
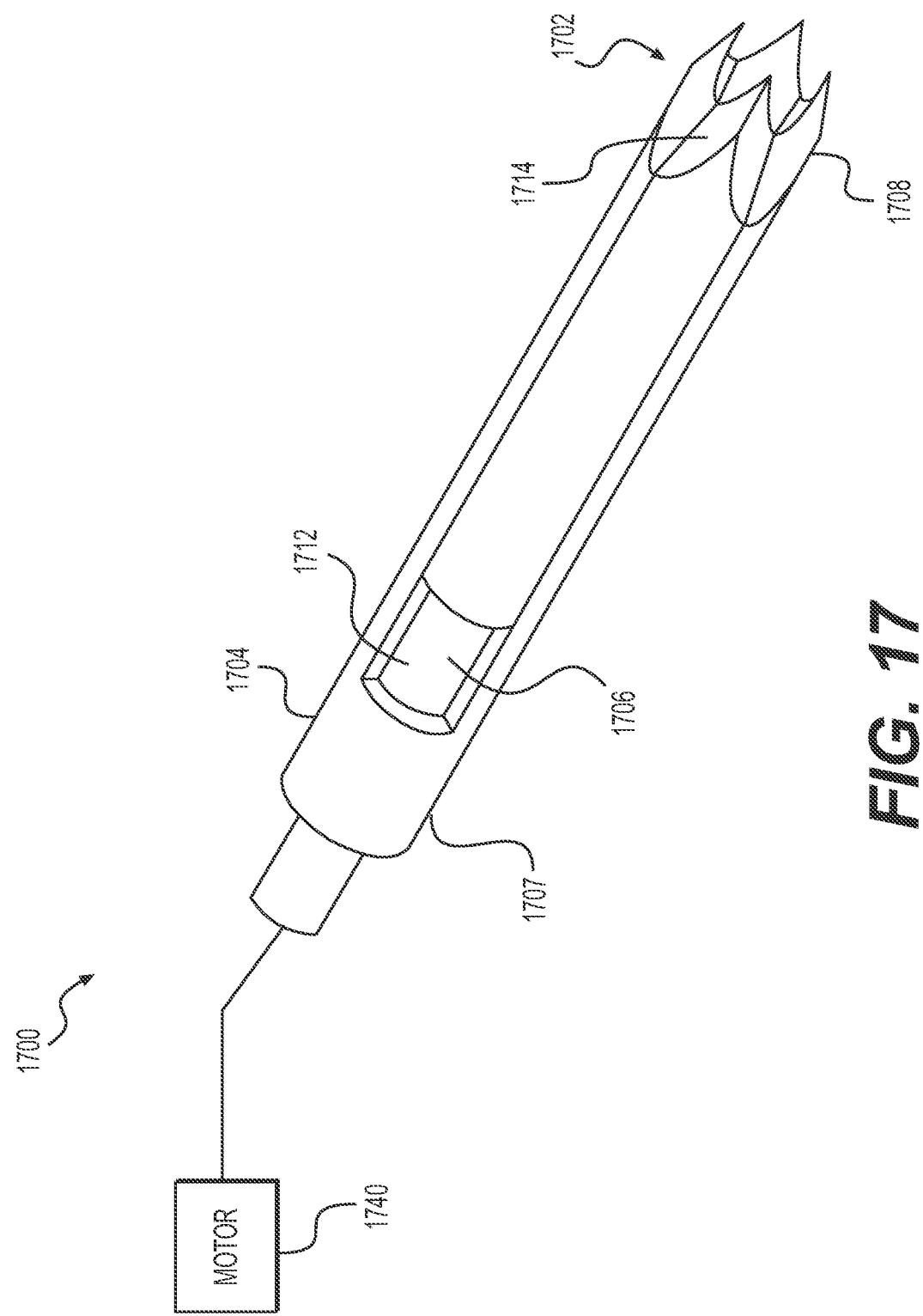
FIG. 17 is a perspective view of a biopsy device according to an example of the present disclosure.

A biopsy device having an oscillating needle 1700 is shown in FIG. 17. Oscillating needle 1700 may include a first assembly 1704 and a second assembly 1706 that each extend from a proximal end of the biopsy device (not shown) to a distal end 1702. First assembly 1704 may include a ring support 1707 and a plurality of piercing tips 1708 that extend distally from ring support 1707. As shown in FIG. 17, first assembly 1704 includes two piercing tips 1708 that are circumferentially spaced from one another about a longitudinal axis of oscillating needle 1700, and whose central longitudinal axes are disposed approximately 180 degrees from one another about the longitudinal axis of oscillating needle 1700. However, it is contemplated that first assembly 1704 may include another suitable number of piercing tips that may be spaced apart from one another at even or uneven intervals. Each piercing tip 1708 may include any of the piercing shapes or geometries set forth above.

Second assembly 1706 may include a rod 1712 and a plurality of piercing tips 1714 that extend distally from rod 1712. Rod 1712 may extend from a proximal end through a lumen defined by ring support 1707, and distally of ring support 1707. Rod 1712 may be hollow, and may be coupled to an aspiration source. Rod 1712 may be longitudinally movable relative to ring support 1707. Piercing tips 1714 may be substantially similar to piercing tips 1708. In the example shown in FIG. 17, second assembly 1706 includes two piercing tips 1714 that are circumferentially spaced from one another about the central longitudinal axis of oscillating needle 1700, and whose central longitudinal axes are disposed approximately 180 degrees from one another about the longitudinal axis of oscillating needle 1700. However, it is contemplated that second assembly 1706 may include another suitable number of piercing tips that may be spaced apart from one another at even or uneven intervals.

When first assembly 1704 and second assembly 1706 are assembled as shown in FIGS. 17-19, first assembly 1704 and second assembly 1706 may be collinear, and piercing tips 1708 and 1714 may alternate circumferentially about the central longitudinal axis, and may be spaced at approximately the same radial distance from the central longitudinal axis. That is, piercing tip 1708 may be adjacent to at least one piercing tip 1714. In the example shown in FIG. 17, each piercing tip 1708 from first assembly 1704 is circumferentially adjacent to two piercing tips 1714 from second assembly 1706. Similarly, each piercing tip 1714 may be circumferentially adjacent to at least one piercing tip 1708, and in the example shown in FIG. 17, each piercing tip 1714 is circumferentially adjacent to two piercings tips 1708. The longitudinal side surfaces of adjacent tips 1708 and 1714 may face one another and may be longitudinally slidable relative to one another. Severed tissue may collect in an internal lumen or cavity disposed radially inward of all of the tips 1708 and 1714.

Figure 20:
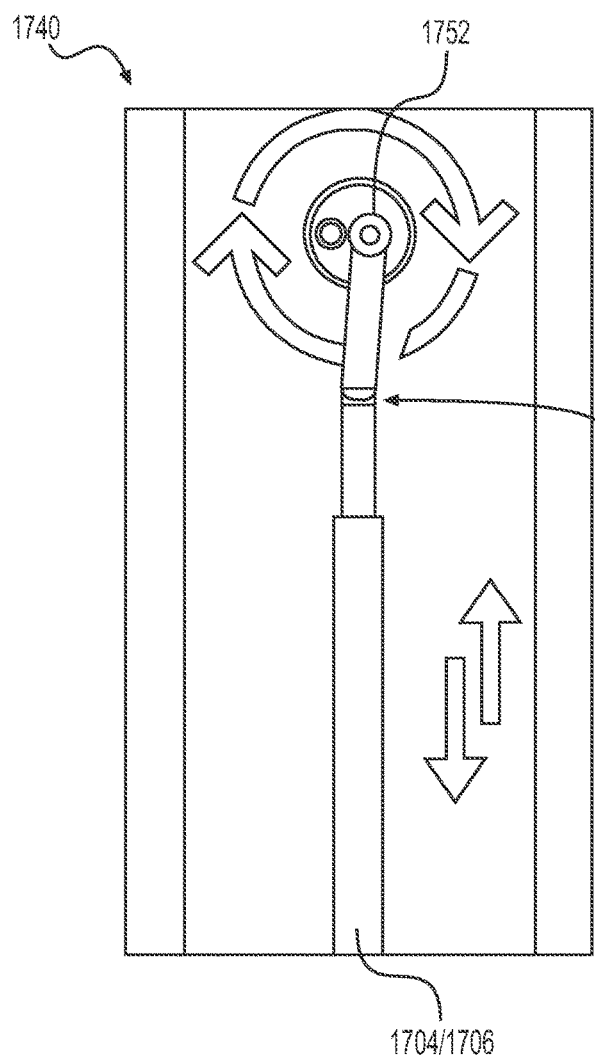
FIGS. 20 and 21 are schematic view illustrations of oscillation drivers according to various examples of the present disclosure.
Figure 21:
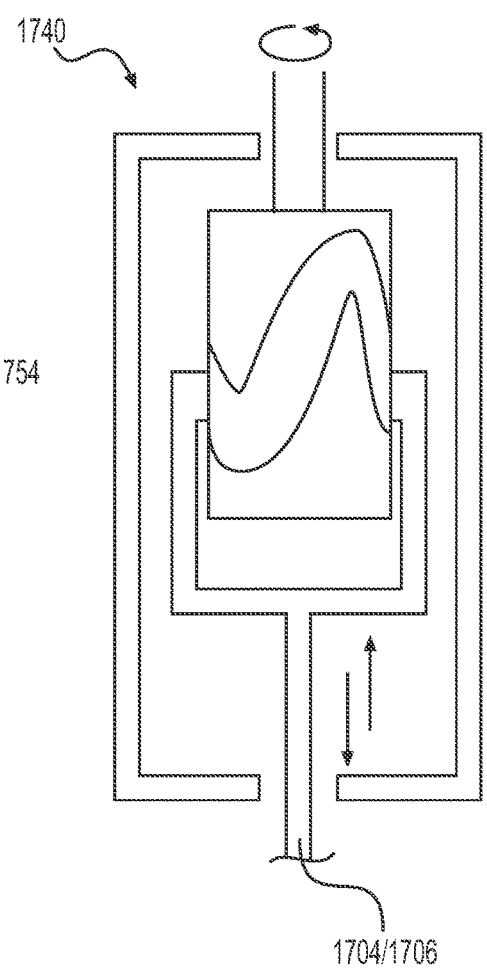

At least one of first assembly 1704 and second assembly 1706 may be coupled to a motor 1740 to drive the oscillation and the relative longitudinal movement between first assembly 1704 and second assembly 1706. In one example shown in FIG. 20, motor 1740 may include an offset axle 1752 having an axis of rotation that is perpendicular to the longitudinal axis of oscillating needle. Offset axle 1752 may be coupled to the proximal end of either first assembly 1704 or second assembly 1706 via a hinged linkage 1754. An alternative embodiment of motor 1740 is shown in FIG. 21, where motor 1740 may be a barrel cam motor having an axis of rotation that is collinear with the longitudinal axis of oscillating needle 1700.

To biopsy tissue disposed radially outward of a body lumen with oscillating needle 1700, the distal end 1702 may be disposed adjacent to tissue surrounding the body lumen. Once in position, motor 1740 may be actuated to cause first assembly 1704 and second assembly 1706 to longitudinally oscillate relative to one another. While oscillating, needle 1700 may be extended distally through tissue, severing the tissue, and directing the tissue proximally through the lumen of second assembly 1706. An aspiration source coupled to the proximal end of needle 1700 may further draw the severed tissue proximally through the needle.

Figure 22:
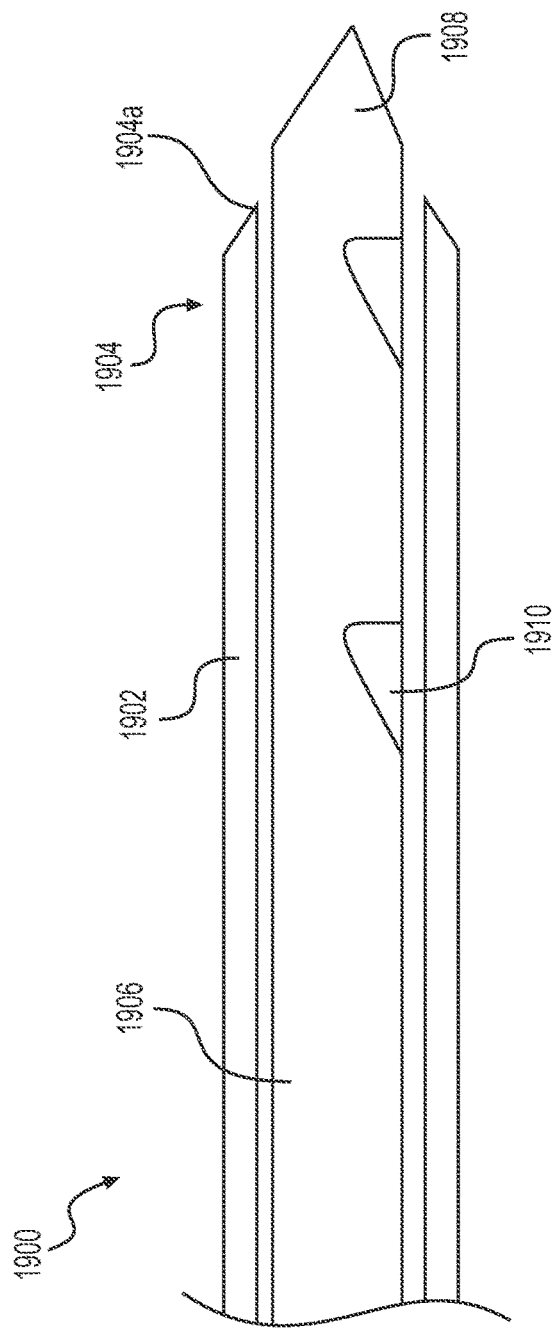
FIGS. 22 and 23 are side view illustrations of a biopsy device according to an example of the present disclosure.
Figure 23:
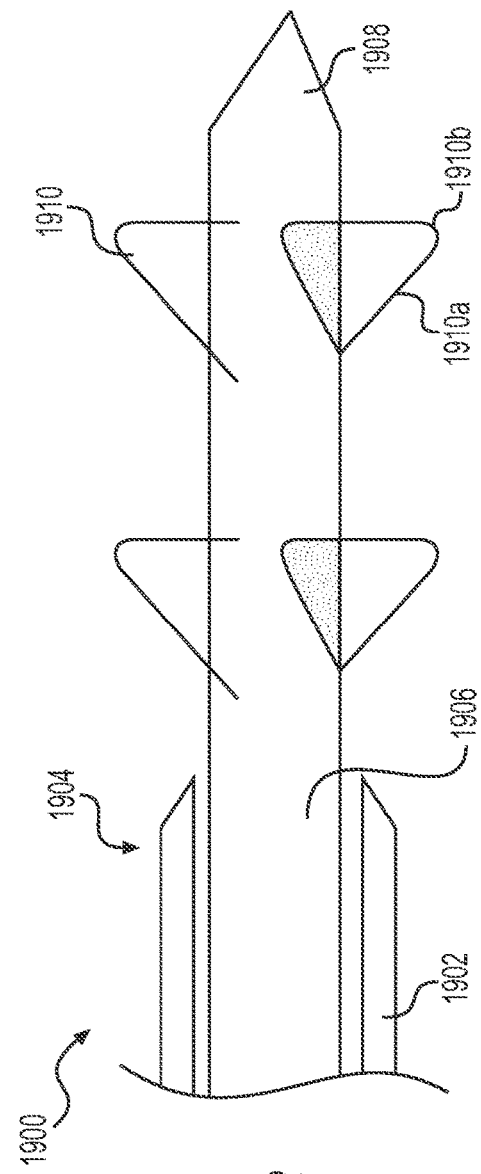

A biopsy device 1900 is shown in FIGS. 22 and 23. Biopsy device 1900 may include a hollow needle 1902 that extends from a proximal end (not shown) toward a distal end 1904. Distal end 1904 may include a sharp circular tip for piercing tissue. A piercing member 1906 may extend through the lumen of hollow needle 1902, and may be longitudinally slidable relative to hollow needle 1902. Piercing member 1906 may include a piercing tip 1908 having any of the piercing shapes or geometries described above, and at least expandable member 1910 that extends radially outward from an outer surface of the piercing member 1906. Each expandable member 1910 may be circumferentially adjacent to at least one opening 1909 disposed through the outer surface of the piercing member 1906 and in communication with a lumen extending through the piercing member 1906.

As shown in FIGS. 22 and 23, piercing member 1906 includes a plurality of expandable members 1910 and a plurality of openings 1909. Expandable member 1910 may include a shape memory material that is biased into a radially-expanded condition. Biopsy device 1900 may be reciprocally movable between a first configuration (shown in FIG. 22) and a second configuration (FIG. 23). In the first configuration, the plurality of expandable members 1910 may be constrained within the lumen of hollow needle 1902, and sit within a corresponding opening 1909, via the inner circumferential surface of hollow needle 1902. Biopsy device 1900 may be transitioned from the first configuration to the second configuration by pulling hollow needle 1902 proximally relative to piercing member 1906, or by pushing piercing member 1906 distally relative to hollow needle 1902. Once piercing member 1906 extends distally past the distal end 1904 of hollow needle 1902, a constraining force acting on expandable members 1910 may be removed, and expandable members 1910 may expand radially outward, exposing openings 1909.

Once expandable members 1910 are in an expanded condition, piercing member 1906 may be rotated to allow expandable members 1910 to cut tissue, and guide the cut tissue into respective circumferentially adjacent openings 1909. Each of the expandable members 1910 may be curved in the circumferential direction and toward an adjacent opening 1909 to facilitate severing tissue when the piercing member 1906 is rotated, and also to serve as a guide for the cut tissue into respective adjacent openings 1909. Once the tissue has been cut by the expandable members 1910 and guided into openings 1909, piercing member 1906 and expandable members 1910 may be retracted within the hollow needle 1902. An aspiration source may be coupled to a proximal end of biopsy device 1900 to move tissue proximally through piercing member 1906, allowing additional tissue to be captured. In some examples, expandable members 1910 may be wing-like flaps that slope proximally and radially-inward along an edge 1910a from an outermost distal point 1910b. The proximally and radially-inward facing edge 1910a may help the expandable members 1910 compress back to a radially-collapsed configuration within the hollow needle 1902, as hollow needle 1902 rides over edges 1910a during movement of hollow needle 1902 distally relative to piercing member 1906.

It will be apparent to those skilled in the art that various modifications and variations may be made in the disclosed systems and processes without departing from the scope of the disclosure. Other examples of the disclosure will be apparent to those skilled in the art from consideration of the specification and practice of the disclosure disclosed herein. It is intended that the specification and examples be considered as exemplary only. The following disclosure identifies some other examples.

We claim:

1. A biopsy device, comprising:
   a first jaw having a first distal tip and a pair of radially-outward facing surfaces forming a radially-outward facing sharp edge in between the pair of radially-outward facing surfaces, wherein the first distal tip is configured to pierce tissue, and the radially-outward facing sharp edge is configured to sever the pierced tissue; and
   a second jaw movable relative to the first jaw between a closed configuration where the first jaw and the second jaw are axially aligned, and an open configuration where the first jaw and the second jaw are offset from one another, the second jaw having a second distal tip proximal to the first distal tip in the closed configuration, the second distal tip is configured to sever the pierced tissue when the second jaw moves relative to the first jaw;
   wherein a collective width of the first jaw and the second jaw when in the closed configuration is equal to a width of the first jaw when in the open configuration.

2. The biopsy device of claim 1, wherein the first jaw is fixed relative to a longitudinal axis of the biopsy device, and the second jaw is movable relative to the longitudinal axis of the biopsy device.

3. The biopsy device of claim 1, wherein both the first jaw and the second jaw are movable relative to a longitudinal axis of the biopsy device.

4. The biopsy device of claim 1, wherein, when viewed from a position distal to the biopsy device along a central longitudinal axis of the biopsy device, the second distal tip is concealed from view by the first jaw.

5. The biopsy device of claim 1, wherein, when viewed from a position distal to the biopsy device along a central longitudinal axis of the biopsy device, an entirety of the second jaw is concealed from view by the first jaw.

6. The biopsy device of claim 1, wherein the first jaw includes a first cavity facing the second jaw, and the second jaw includes a second cavity facing the first jaw, the biopsy device further including a protrusion having a sharp distal tip extending from a base of the first cavity toward the second jaw, and an opening disposed within the second cavity and extending through an outer surface of the second jaw and sized to receive the protrusion.

7. The biopsy device of claim 6, wherein the second jaw includes a sharp outer rim extending about a periphery of the second cavity, and configured to sever the pierced tissue received within the second cavity when the protrusion urges the pierced tissue toward the second cavity.

8. The biopsy device of claim 6, wherein the protrusion aligns with the opening and is configured to push the severed tissue at least partially into the opening when the biopsy device is in the closed configuration.

9. The biopsy device of claim 1, wherein the first distal tip is distally-directed in a first direction and the second distal tip is distally-directed in the first direction when in the closed configuration.

10. The biopsy device of claim 1, wherein the second jaw is radially disposed within the first jaw when in the closed configuration such that an assembled profile of the first jaw and the second jaw is the same as an outer profile of the first jaw when in the open configuration.

11. The biopsy device of claim 10, wherein the first jaw includes an intermediate cavity configured to receive the second jaw when the first jaw and the second jaw are in the closed configuration.

12. The biopsy device of claim 1, wherein the first jaw includes a first length and a first width, and the second jaw includes a second length and a second width; and
    wherein the first length is greater than the second length and the first width is greater than the second width.

13. The biopsy device of claim 1, wherein the pair of radially-outward facing surfaces terminate at the first distal tip such that each of the radially-outward facing surfaces are tapered toward the first distal tip.

14. The biopsy device of claim 13, wherein the second jaw includes a pair of second radially-outward facing surfaces that form at least one second radially-outward-facing sharp edge at an intersection between pair of second radially-outward facing surfaces; and
    wherein the at least one second radially-outward-facing sharp edge is configured to sever the pierced tissue punctured by the first jaw.

15. The biopsy device of claim 14, wherein each of the radially-outward-facing surfaces of the first jaw has a greater surface area than each of the second radially-outward facing surfaces of the second jaw.

16. A biopsy device, comprising:
- a first jaw having a first distal tip and a plurality of radially-outward facing surfaces terminating at the first distal tip, wherein the plurality of radially-outward facing surfaces form at least one radially-outward facing sharp edge at an intersection between each of the plurality of radially-outward facing surfaces, wherein the first distal tip is configured to pierce tissue, and the radially-outward facing sharp edge is configured to sever the tissue pierced by the first distal tip; and
- a second jaw having a second distal tip proximal to the first distal tip, wherein the second jaw is movable relative to the first jaw between a closed configuration and an open configuration, the second distal tip is configured to sever the tissue pierced by the first distal tip.

17. The biopsy device of claim 16, wherein the second jaw is radially disposed within the first jaw when in the closed configuration such that an assembled profile of the first jaw and the second jaw is equal to an outer profile of the first jaw.

18. The biopsy device of claim 16, wherein the second jaw includes an opening disposed through an outer surface of the second jaw, and the opening is configured to allow fluid received within the second jaw to be released out of the second jaw via the opening.

19. A biopsy device, comprising:
- a first jaw having:
  - a first distally-directed tip configured to pierce tissue;
  - a first proximal end including a protrusion configured to grasp tissue, wherein the first distally-directed tip extends transversely relative to the protrusion; and
  - a first center portion positioned between the first distally-directed tip and the first proximal end;
- a second jaw having:
  - a second distally-directed tip configured to contact the first center portion when the first jaw and the second jaw are in a closed configuration; and
  - a second proximal end including an opening that extends through an outer surface of the second jaw, the protrusion being received through the opening to engage tissue positioned between the first jaw and the second jaw when the first jaw and the second jaw are in the closed configuration.

20. The biopsy device of claim 19, wherein a collective width of the first jaw and the second jaw when in the closed configuration is equal to a width of the first jaw when in the open configuration.

* * * * *